(12) United States Patent
Dobrinsky et al.

(10) Patent No.: US 10,525,154 B2
(45) Date of Patent: *Jan. 7, 2020

(54) ULTRAVIOLET TREATMENT OF REGION

(71) Applicant: Sensor Electronic Technology, Inc., Columbia, SC (US)

(72) Inventors: Alexander Dobrinsky, Silver Spring, MD (US); Timothy James Bettles, Irmo, SC (US); Michael Shur, Vienna, VA (US)

(73) Assignee: Sensor Electronic Technology, Inc., Columbia, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/012,954

(22) Filed: Jun. 20, 2018

(65) Prior Publication Data

US 2018/0296712 A1  Oct. 18, 2018

Related U.S. Application Data

(63) Continuation of application No. 15/292,236, filed on Oct. 13, 2016, now Pat. No. 10,004,821.

(60) Provisional application No. 62/240,578, filed on Oct. 13, 2015.

(51) Int. Cl.
  *A61L 2/10* (2006.01)
  *A61L 2/24* (2006.01)
  *A23C 3/07* (2006.01)
  *A61L 2/00* (2006.01)
  *A61L 2/08* (2006.01)

(52) U.S. Cl.
  CPC ............... *A61L 2/10* (2013.01); *A23C 3/076* (2013.01); *A61L 2/0047* (2013.01); *A61L 2/088* (2013.01); *A61L 2/24* (2013.01); *A61L 2202/14* (2013.01); *A61L 2202/21* (2013.01); *A61L 2202/22* (2013.01); *A61L 2202/24* (2013.01)

(58) Field of Classification Search
  CPC .......... A61L 2/10; A61L 2/24; A61L 2202/14; A61L 2202/24
  USPC ...... 250/428, 432 R, 435, 436, 492.1, 492.2, 250/492.3
  See application file for complete search history.

(56) References Cited

U.S. PATENT DOCUMENTS

| 7,553,456 B2 | 6/2009 | Gaska et al. |
| 7,634,996 B2 | 12/2009 | Gaska et al. |
| 8,277,734 B2 | 10/2012 | Koudymov et al. |

(Continued)

OTHER PUBLICATIONS

Chang, H., U.S. Appl. No. 15/292,236, Office Action1, dated Aug. 25, 2017, 18 pages.

(Continued)

*Primary Examiner* — Nicole M Ippolito
*Assistant Examiner* — Hanway Chang
(74) *Attorney, Agent, or Firm* — LaBatt, LLC

(57) ABSTRACT

A system for providing ultraviolet treatment to light absorbing liquids, such as biological liquids in a medical instrument, is disclosed. The system can include an ultraviolet impenetrable housing configured to enclose a portion of the medical instrument containing the biological fluid. At least one ultraviolet radiation source is integrated within the housing that emits ultraviolet radiation towards the medical instrument and the biological fluid. A control unit is configured to direct the ultraviolet radiation source to treat the biological fluid with ultraviolet radiation.

20 Claims, 12 Drawing Sheets

(56) References Cited

U.S. PATENT DOCUMENTS

| | | |
|---|---|---|
| 8,980,178 B2 | 3/2015 | Gaska et al. |
| 9,006,680 B2 | 4/2015 | Bettles et al. |
| 9,061,082 B2 | 6/2015 | Gaska et al. |
| 9,138,499 B2 | 9/2015 | Bettles et al. |
| 9,179,703 B2 | 11/2015 | Shur et al. |
| 9,572,903 B2 | 2/2017 | Dobrinsky et al. |
| 9,603,960 B2 | 3/2017 | Dobrinsky et al. |
| 9,687,577 B2 | 6/2017 | Dobrinsky et al. |
| 9,718,706 B2 | 8/2017 | Smetona et al. |
| 10,004,821 B2 * | 6/2018 | Dobrinsky ............... A61L 2/10 |
| 2007/0272877 A1 | 11/2007 | Tribelsky et al. |
| 2013/0048545 A1 | 2/2013 | Shatalov et al. |
| 2014/0060094 A1 | 3/2014 | Shur et al. |
| 2014/0060095 A1 | 3/2014 | Shur et al. |
| 2014/0060096 A1 | 3/2014 | Shur et al. |
| 2014/0060104 A1 | 3/2014 | Shur et al. |
| 2014/0202962 A1 | 7/2014 | Bilenko et al. |
| 2015/0008167 A1 | 1/2015 | Shturm et al. |
| 2015/0069265 A1 | 3/2015 | Smetona et al. |
| 2015/0069270 A1 | 3/2015 | Shur et al. |
| 2015/0165079 A1 | 6/2015 | Shur et al. |
| 2015/0217011 A1 | 8/2015 | Bettles et al. |
| 2015/0297767 A1 | 10/2015 | Gaska et al. |
| 2015/0336810 A1 | 11/2015 | Smetona et al. |
| 2016/0000953 A1 | 1/2016 | Bettles et al. |
| 2016/0058020 A1 | 3/2016 | Shur et al. |
| 2016/0114186 A1 | 4/2016 | Dobrinsky et al. |
| 2016/0128526 A1 | 5/2016 | Dobrinsky et al. |
| 2016/0324996 A1 | 11/2016 | Bilenko et al. |
| 2017/0057842 A1 | 3/2017 | Dobrinsky et al. |
| 2017/0100494 A1 | 4/2017 | Dobrinsky et al. |

OTHER PUBLICATIONS

Chang, H., U.S. Appl. No. 15/292,236, Notice of Allowane, dated Feb. 28, 2018, 8 pages.

* cited by examiner

ULTRAVIOLET TREATMENT OF REGION

REFERENCE TO RELATED APPLICATIONS

The present patent application is a continuation of U.S. application Ser. No. 15/292,236, filed on 13 Oct. 2016, which claims the benefit of U.S. Provisional Application No. 62/240,578, filed on 13 Oct. 2015, each of which is hereby incorporated by reference in its entirety to provide continuity of disclosure.

TECHNICAL FIELD

The disclosure relates generally to ultraviolet treatment, and more specifically, to a solution for using ultraviolet radiation for treating (e.g., disinfecting, sterilizing, sanitizing, and/or the like) light absorbing fluids, such as biological fluids.

BACKGROUND ART

Liquid treatment using ultraviolet radiation offers many advantages over other forms of liquid treatment, such as chemical treatment. For example, treatment with ultraviolet radiation does not introduce additional chemical or biological contaminants into the liquid. More specifically, the introduction of chemical components can be hazardous for treatment of medical or biological liquids. Furthermore, ultraviolet radiation provides one of the most efficient approaches to decontamination since there are no microorganisms known to be resistant to ultraviolet radiation, unlike other decontamination methods such as chlorination. Ultraviolet radiation is known to be highly effective against bacteria, viruses, algae, molds and yeasts. For example, a hepatitis virus has been shown to survive for considerable periods of time in the presence of chlorine, but is readily eliminated by ultraviolet radiation treatment. The removal efficiency of ultraviolet radiation for most microbiological contaminants such as bacteria and viruses generally exceeds 99%. To this extent, ultraviolet radiation is highly efficient in eliminating *E-coli, Salmonella*, Typhoid fever, Cholera, Tuberculosis, an Influenza Virus, a Polio Virus, and a Hepatitis A Virus.

Intensity, radiation wavelength, and duration of radiation are all parameters that have a role in determining the disinfection rate provided by the ultraviolet radiation treatment. These parameters can vary based on a particular target culture. A proper setting of these parameters can ensure that the ultraviolet radiation does not allow microorganisms to develop an immune response, unlike the case with chemical treatments. Furthermore, the parameters set for the ultraviolet radiation will affect biological agents by fusing and damaging the DNA of microorganisms, and preventing their replication. If a sufficient amount of a protein is damaged in a cell of a microorganism, the cell enters apoptosis or a programmed death.

Ultraviolet radiation disinfection using mercury based lamps is a well-established technology that has been used with ultraviolet treatment systems. In general, an ultraviolet treatment system for treating water using ultraviolet radiation is relatively easy to install and maintain in a plumbing or septic system. Use of ultraviolet radiation in such systems does not affect the overall system. However, it is often desirable to combine an ultraviolet purification system with another form of filtration since the ultraviolet radiation cannot neutralize chlorine, heavy metals, and other chemical contaminants that may be present in the liquid. Various membrane filters for sediment filtration, granular activated carbon filtering, reverse osmosis, and/or the like, can be used as a filtering device to reduce the presence of chemicals and other inorganic contaminants.

Mercury lamp-based ultraviolet radiation treatment systems have several shortcomings when compared to deep ultraviolet (DUV) light emitting device (LED)-based technologies, particularly with respect to certain disinfection applications. For example, in rural and/or off-grid locations, it is desirable for an ultraviolet purification system to have one or more various attributes such as: a long operating lifetime, contain no hazardous components, not be readily susceptible to damage, require minimal operational skills, have no required special disposal procedures, be capable of operating on local intermittent electrical power, and/or the like. Use of a DUV LED-based solution can provide a solution that improves one or more of these attributes as compared to a mercury vapor lamp-based approach. For example, in comparison to mercury vapor lamps, DUV LEDs can have substantially longer operating lifetimes (e.g., by a factor of ten); do not include hazardous components (e.g., mercury), which require special disposal and maintenance; are more durable in transit and handling (e.g., no filaments or glass); have a faster startup time; have a lower operational voltage; are less sensitive to power supply intermittency; are more compact and portable; can be used in moving devices; can be powered by photovoltaic (PV) technology, which can be installed in rural locations having no continuous access to electricity and having scarce resources of clean water; and/or the like.

SUMMARY OF THE INVENTION

This Summary Of The Invention introduces a selection of certain concepts in a brief form that are further described below in the Detailed Description Of The Invention. It is not intended to exclusively identify key features or essential features of the claimed subject matter set forth in the Claims, nor is it intended as an aid in determining the scope of the claimed subject matter.

Aspects of the present invention are directed to a system for providing an ultraviolet treatment of light absorbing fluids that can include biological fluids, such as medical fluids, which may need removal of bacteria, viruses, germs, and the like. The ultraviolet treatment system of the embodiments described herein can treat the biological fluids in medical instruments or devices used to transport, deliver and remove the fluids. Examples of these types of medical instruments or devices can include, but are not limited to, catheters, tubing, syringes, surgical tools, needles, etc. The ultraviolet treatment system can also treat biological fluids in medical instruments or devices that are used to store or contain the fluids such as for example, medical receptacles like infusion bags, glass containers and plastic containers.

The ultraviolet treatment system of the illustrative embodiments described herein can include an ultraviolet impenetrable housing configured to enclose a portion of a medical instrument containing a biological fluid. In one embodiment, the housing can include a first half-cylinder portion, a second half-cylinder portion, and a fastener that couples the first half-cylinder portion to the second half-cylinder portion, forming an extendible insertion opening there between to receive and secure the medical instrument. In another embodiment, the housing can include a flexible sleeve that is configured to wrap around the medical instrument and be secured wrapped there around. In still another embodiment, the housing can include an outer chamber and an inner chamber enclosed by the outer chamber. In one embodiment, the inner chamber can have a first inner chamber and a second inner chamber surrounding the first inner chamber, wherein the first inner chamber has an inflow connection and an outflow connection with the biological fluid. A medical instrument connector can be used to couple the inner chamber with the medical instrument. For example, the medical instrument connector can have a first end that couples to the inner chamber and a second end that couples to the medical instrument.

The ultraviolet treatment system of the illustrative embodiments described herein can include an ultraviolet light emitting diode (UV LED) based system integrated with the housing that provides an ultraviolet treatment to the biological fluids. In particular, the UV LED based system can employ at least one UV LED source operating at a wavelength that ranges from about 260 nanometers (nm) to about 310 nm, with 250 nm to 290 nm being a preferred range for facilitating disinfection, sterilization and the like, of the biological fluids.

Optical elements can be used in conjunction with the UV LED based system to direct and redirect ultraviolet radiation emitted from the UV LED source(s) toward the medical instrument and the biological fluid therein. In the various illustrative embodiments described herein, the optical element can be integrated within the housing. For example, in one embodiment, a parabolic mirror element, an omnidirectional mirror, a planar mirror, and/or the like can be formed on an inner surface of the housing. Other examples of optical elements that can be deployed in the housing can include lenses, prismatic ultraviolet transparent elements, and/or the like. In another embodiment, a wave guiding layer can be formed on an inner surface of the housing to deliver light to a particular section of the medical instrument. In still another embodiment, the inner surface of the housing can include ultraviolet reflective material. In a further embodiment, in which the housing includes an inner chamber and an outer chamber, ultraviolet reflective domains or ultraviolet transparent domains can be located between the inlet port and the outlet port to provide a porous ultraviolet transparent, motion generating media there between.

The ultraviolet treatment system can also include a pre-treatment component configured to treat the biological fluid prior to entering the housing. The pre-treatment component can include a filtering element that removes undesired contaminants from the fluid, such as a biological fluid. The pre-treatment component can also include an ultraviolet transparent enclosure having an inlet port and an outlet port for transporting the biological fluid there through. The pre-treatment component can further include at least one pre-treatment ultraviolet radiation source located about the ultraviolet transparent enclosure to pre-treat the biological fluid with ultraviolet radiation. In one embodiment, pre-treatment channels can be placed in the ultraviolet transparent enclosure to transport the biological fluid from the outlet port to the inlet port. In another embodiment, the pre-treatment component can include ultraviolet reflective domains or ultraviolet transparent domains located between the inlet port and the outlet port to provide a porous ultraviolet transparent media adapted to create motion of the ultraviolet radiation.

The ultraviolet treatment system can also include a control unit to control the ultraviolet treatment of the biological fluids. For example, the control unit can direct the ultraviolet radiation source to treat the biological fluid with ultraviolet radiation. The control unit can direct the ultraviolet radiation source by controlling a plurality of operating parameters for treating the biological fluids. The operating parameters can include a wavelength of the ultraviolet radiation that is emitted from the ultraviolet radiation source, an intensity or dosage of the ultraviolet radiation delivered to the biological fluid by the ultraviolet radiation source and a treatment time that the ultraviolet radiation source delivers the ultraviolet radiation to the biological fluid. Other parameters can include a power setting for operating the ultraviolet radiation source, and a maximum operating temperature of the ultraviolet radiation source.

Other components that may be utilized with the ultraviolet treatment system can include a timer, an input component, an output component and a power supply. The timer can be set in accordance with the specified treatment time in order to ensure that the ultraviolet radiation source delivers a sufficient dosage for the corresponding treatment directed to the medical instrument and the biological fluid. The input component can permit a user to adjust at least one of the plurality of operating parameters and the output component can indicate status information of the treatment (e.g., on, off, treated, needs treatment, etc.). The power supply can provide power to all of the components of the ultraviolet treatment system to facilitate the treatment of the medical instrument and the biological fluid.

A first aspect of the invention provides a system, comprising: an ultraviolet impenetrable housing configured to enclose a portion of a medical instrument containing a biological fluid; at least one ultraviolet radiation source integrated within the housing that is configured to emit ultraviolet radiation towards the medical instrument and the biological fluid therein; a control unit configured to direct the ultraviolet radiation source to treat the biological fluid with ultraviolet radiation, the control unit controlling a plurality of operating parameters for treating the biological fluids, the operating parameters including a wavelength of the ultraviolet radiation emitted from the ultraviolet radiation source, an intensity of the ultraviolet radiation delivered to the biological fluid by the ultraviolet radiation source and a treatment time that the ultraviolet radiation source delivers the ultraviolet radiation to the biological fluid; an input component that permits a user to adjust at least one of the plurality of operating parameters; and an output component that provides status information of the treatment of the biological fluid.

A second aspect of the invention provides a system, comprising: an ultraviolet impenetrable housing configured to enclose a portion of a medical instrument containing a biological fluid, wherein the housing comprises an outer chamber and an inner chamber enclosed by the outer chamber, the inner chamber having a first inner chamber and a second inner chamber surrounding the first inner chamber, the first inner chamber having an inflow connection and an outflow connection with the biological fluid; a medical instrument connector configured for coupling the inner chamber with the medical instrument, the medical instrument connector having a first end that couples to the inner chamber and a second end that couples to the medical instrument; at least one ultraviolet radiation source integrated within the housing that is configured to emit ultraviolet radiation towards the medical instrument and the biological fluid therein, wherein the ultraviolet radiation source is located on a wall of the outer chamber and oriented to emit ultraviolet radiation to the inner chamber; a control unit configured to direct the ultraviolet radiation source to treat the biological fluid with ultraviolet radiation, the control unit controlling a plurality of operating parameters for treating the biological fluids, the operating parameters including a wavelength of the ultraviolet radiation emitted from the ultraviolet radiation source, an intensity of the ultraviolet radiation delivered to the biological fluid by the ultraviolet radiation source and a treatment time that the ultraviolet radiation source delivers the ultraviolet radiation to the biological fluid; an input component that permits a user to adjust at least one of the plurality of operating parameters; and an output component that provides status information of the treatment of the biological fluid.

A third aspect of the invention provides a system, comprising: an ultraviolet impenetrable housing configured to enclose a portion of a medical instrument containing a biological fluid, the housing having a first half-cylinder portion, a second half-cylinder portion, and a fastener that couples the first half-cylinder portion to the second half-cylinder portion, forming an extendible insertion opening there between to receive and secure the medical instrument; at least one ultraviolet radiation source integrated within the housing that is configured to emit ultraviolet radiation towards the medical instrument and the biological fluid therein to provide an ultraviolet treatment thereof; a control unit configured to direct the ultraviolet radiation source to treat the biological fluid with ultraviolet radiation, the control unit controlling a plurality of operating parameters for treating the biological fluids, the operating parameters including a wavelength of the ultraviolet radiation emitted from the ultraviolet radiation source, an intensity of the ultraviolet radiation delivered to the biological fluid by the ultraviolet radiation source and a treatment time that the ultraviolet radiation source delivers the ultraviolet radiation to the biological fluid; an input component that permits a user to adjust at least one of the plurality of operating parameters; and an output component that provides status information of the treatment of the biological fluid.

A fourth aspect of the invention provides a pre-treatment device to pre-treat biological fluid prior to entering an ultraviolet treatment system, comprising: an ultraviolet transparent enclosure having an inlet port and an outlet port for transporting the biological fluid there through, wherein the ultraviolet transparent enclosure includes one of a plurality of pre-treatment channels to transport the biological fluid from the outlet port to the inlet port and one of a plurality of ultraviolet reflective domains or ultraviolet transparent domains located between the inlet port and the outlet port to provide a porous ultraviolet transparent, motion generating media there between; a filter element to remove undesired contaminants from the biological fluid; at least one pre-treatment ultraviolet radiation source located about the ultraviolet transparent enclosure that is configured to pre-treat the biological fluid with ultraviolet radiation; a control unit configured to direct the pre-treatment ultraviolet radiation source to treat the biological fluid with ultraviolet radiation, the control unit controlling a plurality of operating parameters for pre-treating the biological fluids, the operating parameters including a wavelength of the ultraviolet radiation emitted from the ultraviolet radiation source, an intensity of the ultraviolet radiation delivered to the biological fluid by the pre-treatment ultraviolet radiation source and a treatment time that the pre-treatment ultraviolet radiation source delivers the ultraviolet radiation to the biological fluid; an input component that permits a user to adjust at least one of the plurality of operating parameters; and an output component that provides status information of the treatment of the biological fluid.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 1A:
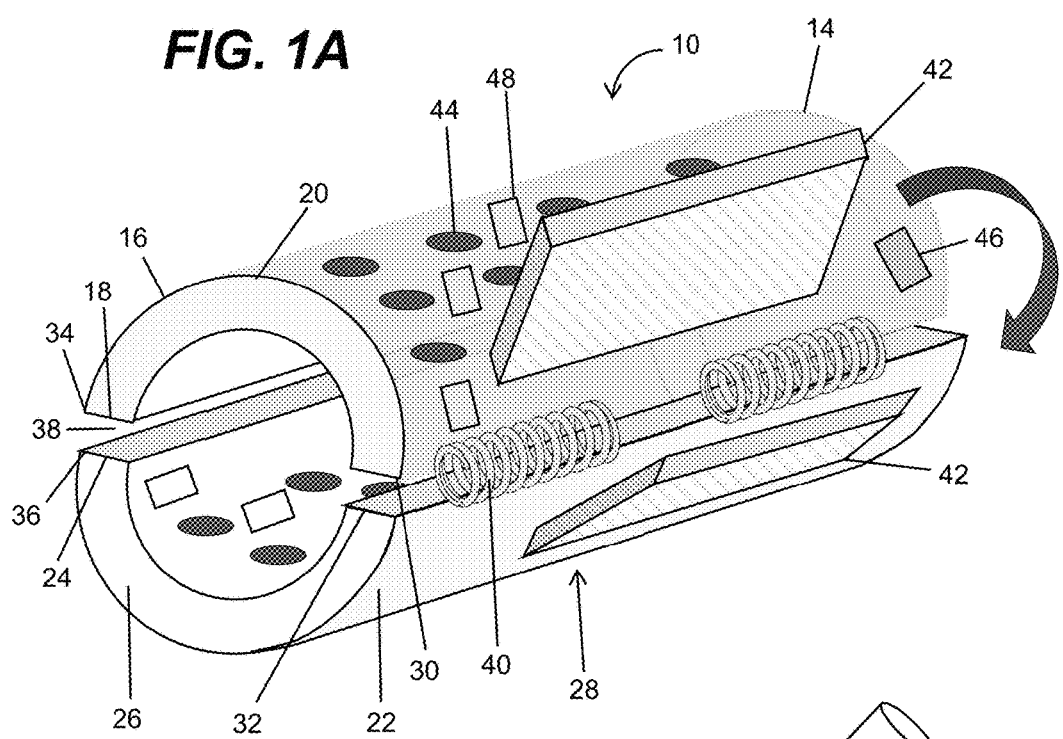
FIGS. 1A-1B show schematic views of an illustrative ultraviolet treatment system for treating a biological fluid in a medical instrument according to an embodiment.

As indicated above, aspects of the invention are directed to an ultraviolet system for providing an ultraviolet treatment of light absorbing fluids, such as biological fluids that may need removal of bacteria, viruses, germs, and the like. As used herein, biological fluids means any bio-organic fluid produced by an organism that can be excreted, secreted, obtained or developed as a result of a pathological process. A non-exhaustive list of biological fluids can include blood, cerebrospinal fluid, pleural fluid, sweat, tears, milk. As used herein, biological fluids is also intended to cover medical fluids that are developed for and used in individual life forms. A non-exhaustive list of medical fluids that is intended herein to be covered by the term biological fluid can include insulin, feed solutions, and injectable and intravenously supplied medication.

The ultraviolet treatment system can treat biological fluids in medical instruments or devices used to transport, deliver and remove the fluids. Examples of medical instruments or devices can include, but are not limited to, catheters, tubing, syringes, surgical tools, needles, etc. The ultraviolet treatment system can also treat biological fluids in medical instruments or devices that are used to store or contain the fluids such as for example, medical receptacles like infusion bags, glass containers and plastic containers.

As used herein, an ultraviolet treatment of a biological fluid and the medical instrument containing the fluid can entail sanitizing, disinfecting, and/or sterilizing. Sanitizing generally means reducing the number of bacterial contaminants to a predetermined safe level. Disinfecting generally means destroying pathogenic and other types of microorganisms, while sterilizing can be more extensive in that it kills all microbial forms and/or include destroying the ability of the microbial forms to reproduce.

Ultraviolet radiation, which can be used interchangeably with ultraviolet light, means electromagnetic radiation having a wavelength ranging from approximately 10 nm to approximately 400 nm. Within this range, there is ultraviolet-A (UV-A) electromagnetic radiation having a wavelength ranging from approximately 315 nm to approximately 400 nm, ultraviolet-B (UV-B) electromagnetic radiation having a wavelength ranging from approximately 280 nm to approximately 315 nm, and ultraviolet-C (UV-C) electromagnetic radiation having a wavelength ranging from approximately 100 nm to approximately 280 nm.

Generally, ultraviolet radiation, and in particular, UV-B radiation and UV-C radiation is "germicidal," i.e., it deactivates the DNA of bacteria, viruses and other pathogens, and thus, destroys their ability to multiply and cause disease. This effectively results in sterilization of the microorganisms. Specifically, UV-B radiation and UV-C radiation cause damage to the nucleic acid of microorganisms by forming covalent bonds between certain adjacent bases in the DNA. The formation of these bonds prevents the DNA from being "unzipped" for replication, and the organism is neither able to produce molecules essential for life process, nor is it able to reproduce. In fact, when an organism is unable to produce these essential molecules or is unable to replicate, it dies. Ultraviolet radiation with a wavelength of approximately between about 250 nm to about 280 nm provides the highest germicidal effectiveness, while an ultraviolet radiation between about 260 nm to about 310 nm is sufficient for providing overall germicidal effectiveness of medical devices and equipment, and ultraviolet radiation between 250 nm to 290 nm is a preferred range for facilitating disinfection, sterilization of the biological fluids. While susceptibility to ultraviolet radiation varies, exposure to ultraviolet energy in the above range for about 20 to about 34 milliwatt-seconds/cm$^2$ is adequate to deactivate approximately 99 percent of the pathogens.

As used herein, a material/structure is considered to be "reflective" to ultraviolet light of a particular wavelength when the material/structure has an ultraviolet reflection coefficient of at least 30 percent for the ultraviolet light of the particular wavelength. A highly ultraviolet reflective material/structure has an ultraviolet reflection coefficient of at least 80 percent. Furthermore, a material/structure/layer is considered to be "transparent" to ultraviolet radiation of a particular wavelength when the material/structure/layer allows at least ten percent of radiation having a target wavelength, which is radiated at a normal incidence to an interface of the material/structure/layer to pass there through. Also, unless otherwise noted, the term "set" means one or more (i.e., at least one) and the phrase "any solution" means any now known or later developed solution.

The ultraviolet treatment systems described herein can include a number of components described below in more detail, some of which may be optional, that facilitate the treatment of biological fluids and the medical instruments in which the fluids can be located. The modalities used with the various ultraviolet treatment systems described herein including its respective components can include any now known or later developed approaches that incorporate the concepts of the embodiments described below in more detail.

Figure 1B:
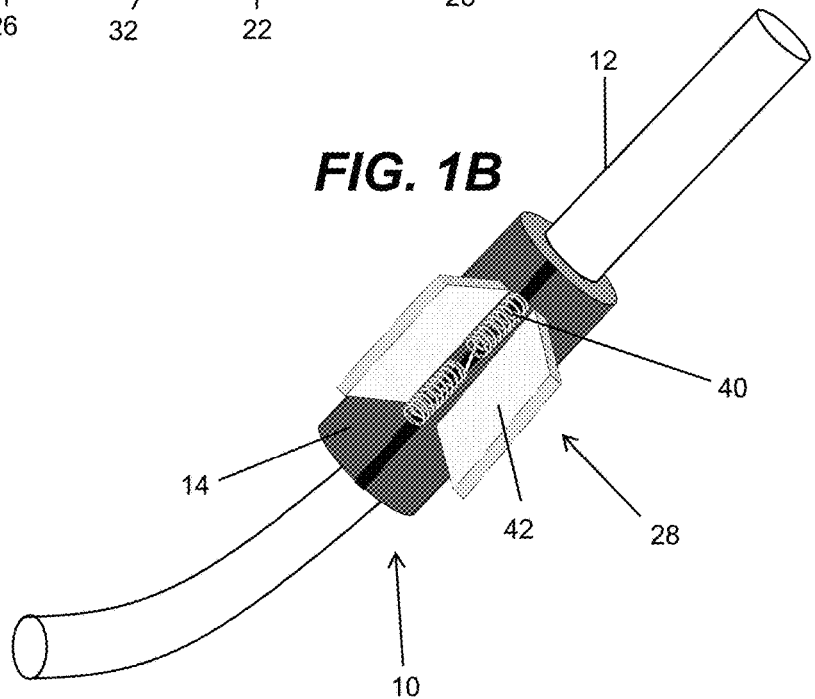

Turning to the drawings, FIGS. 1A-1B show schematic views of an ultraviolet treatment system 10 for treating a biological fluid in a medical instrument 12 according to an embodiment. In this embodiment, the medical instrument can include a catheter. Although the medical instrument 12 in this embodiment is noted as a catheter, the ultraviolet treatment system 10 is suitable for use with other similar sized medical instruments and devices that can transport or distribute biological fluids such as medical tubing, needles, syringes and/or the like.

The ultraviolet treatment system 10 of FIGS. 1A-1B can include an ultraviolet impenetrable housing 14 configured to enclose a portion of the medical instrument 12 containing a biological fluid. In one embodiment, the housing can include a first half-cylinder portion 16 having a rectangular surface 18 and a curved outer surface 20, a second half-cylinder portion 22 having a rectangular surface 24 and a curved outer surface 26. A fastener 28 can couple the first half-cylinder portion 16 to the second half-cylinder portion 22. In one embodiment, the fastener 28 can couple a first side 30 of the rectangular surface 18 of the first half-cylinder 16 to a first side 32 of the rectangular surface 24 of the second half-cylinder 22. In this manner, a second side 34 of the rectangular surface 18 of the first half-cylinder 16 is unfastened from a second side 36 of the rectangular surface 24 of the second half-cylinder 22 to form an extendible insertion opening 38 to receive the medical instrument 12.

In one embodiment, the fastener 28 can include a spring element 40 and wing assembly 42. The spring element 40 can couple the first side 30 of the rectangular surface 18 of the first half-cylinder 16 to the first side 32 of the rectangular surface 24 of the second half-cylinder 22. The wing assembly 42 can comprise a first wing 42 located on the curved outer surface 20 of the first half-cylinder 16 and a second wing 42 located on the curved outer surface 26 of the second half-cylinder 22. The first and second wings 42 are operatively engaged with the spring element 40, wherein an inward pressure applied to the wings engages the spring element to separate the second side 34 of the rectangular surface 18 of the first half-cylinder 16 from the second side 36 of the rectangular surface 24 of the second half-cylinder 22. As a result, the insertion opening 38 can expand to receive the medical instrument 12. With the pressure removed from the wing assembly 42, the insertion opening contracts, such that the second side 34 of the rectangular surface 18 of the first half-cylinder 16 moves towards and abuts with the second side 36 of the rectangular surface 24 of the second half-cylinder 22, to secure the medical instrument 12 in the opening 38 of the housing 14.

Although the fastener 28 is depicted in FIGS. 1A-1B as a spring element 40 and wing assembly 42 it is understood that other types of fasteners can be used to secure the medical instrument 12 within the housing 14. For example, the fastener 28 can include clips, holders, binders, tabs, magnetic coupling, hook and loop fasteners, mechanical fasteners (e.g., threaded connections), friction type fasteners placed between two surfaces, etc.

In order to accommodate medical instruments 12 of varying shapes and sizes (e.g., diameters), the housing 14 can include an expandable and compressible material, such as an elastomer. Other materials can include, for example, rubber having an internal surface with an ultraviolet reflective property, e.g., through deposition of aluminum thereon. In the embodiment depicted in FIGS. 1A-1B, half-cylinders of rubber can provide additional (better/adequate) grip with the medical instrument.

FIG. 1A shows that the ultraviolet treatment system 10 can have at least one ultraviolet radiation source 44 integrated within the housing 14. Each ultraviolet radiation source 44 is configured to emit ultraviolet radiation towards a surface of the medical instrument 12 to effectuate an ultraviolet treatment of the biological fluid therein. In the example illustrated in FIGS. 1A-1B, the ultraviolet radiation sources 44 can be integrated with one or both of the half-cylinder 16, 22 that formed the housing 14. For example, the ultraviolet radiation sources 44 can be integrated in the interior portions of the curved outer surfaces 20, 26 of the half-cylinder 16, 22, respectively.

The set of ultraviolet radiation sources 44 can comprise any combination of one or more ultraviolet radiation emitters. Examples of ultraviolet radiation emitters can include, but are not limited to, high intensity ultraviolet lamps (e.g., high intensity mercury lamps), discharge lamps, ultraviolet light emitting diodes (UV LEDs), super luminescent LEDs, laser diodes, and/or the like. In one embodiment, the set of ultraviolet radiation sources 44 can include a set of LEDs manufactured with one or more layers of materials selected from the group-III nitride material system (e.g., $Al_xIn_yGa_{1-x-y}N$, where $0 \le x$, $y \le 1$, and $x+y \le 1$ and/or alloys thereof). Additionally, the set of ultraviolet radiation sources 44 can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like. Illustrative wave guiding structures include, but are not limited to, a wave guide, a plurality of ultraviolet fibers, each of which terminates at an opening, a diffuser, and/or the like.

It is understood that the number of ultraviolet radiation sources 44 illustrated in FIG. 1A and the other various embodiments described herein is only illustrative. Those skilled in the art will appreciate any number of ultraviolet radiation sources 44 may be located within the housing 14. For example, the housing 14 can have only one ultraviolet radiation source 44 or multiple ultraviolet radiation sources 44 can be located at the same position along an inner surface of the housing (e.g. a central portion) or at varying locations.

In order to effectuate an ultraviolet treatment of the biological fluid in the medical instrument 12, it is understood that the medical instrument should have a transparency to ultraviolet light, allowing the feasibility of irradiating biological fluid within the instrument. For example, medical instruments including fluoropolymer material, which in general, has a high transparency to ultraviolet light, are well suited for use with any of the embodiments described herein.

The ultraviolet radiation sources 44 can be configured to be operated at a number of wavelengths. For example, in one embodiment, the ultraviolet radiation sources 44 can be configured to operate at a wavelength that ranges from about 260 nm to about 310 nm, with 250 nm to 290 nm being a preferred range. Emission of ultraviolet light within these ranges for a predetermined time period is sufficient to effectively treat the biological fluids from a disinfection and sterilization point of view.

In one embodiment, the ultraviolet radiation sources 44 can be configured to function in a coordinated manner. For example, the ultraviolet radiation sources 44 can operate at the same wavelengths and intensities for the same duration, or the sources can operate at different wavelengths and intensity for varying durations. In one embodiment, a first set of ultraviolet radiation sources 44 can operate at a target wavelength and intensity that is designed for the disinfection of one type of bacteria and/or viruses, while a second set of ultraviolet radiation sources 44 can operate at a different target wavelength and intensity that is designed for disinfection of a different type of bacteria and/or viruses.

In order to recycle or recirculate the ultraviolet radiation emitted from the ultraviolet radiation sources 44, all of the inner surface of the housing 14 or at least a portion thereof can have an ultraviolet reflective layer formed on an ultraviolet impenetrable material (e.g., ultraviolet absorbing material) that forms an exterior surface of the housing. An ultraviolet reflective layer with a reflection coefficient of at least 50% will enable recycling of the ultraviolet radiation generation from the ultraviolet radiation sources 44. In one embodiment, the ultraviolet reflective layer can include a diffusive ultraviolet reflective layer. The diffusive ultraviolet reflective layer can include a coating or thin film of a fluoropolymer. Examples of a fluoropolymer that are suitable as an ultraviolet reflective material that enables diffusive reflectivity can include, but are not limited to, expanding polytetrafluoroethylene (ePTFE) membrane (e.g., GORE® DRP® Diffuse Reflector Material), polytetrafluoroethylene (PTFE), and/or the like.

Although not shown in detail in FIGS. 1A-1B, the ultraviolet treatment system 10 in this embodiment and others described herein can include a multitude of components that effectuate an ultraviolet treatment of biological fluid in the medical device 12. For example, the ultraviolet treatment system 10 can include a control unit 46 that is configured to direct the ultraviolet radiation sources 46 to treat the biological fluid with ultraviolet radiation. In the embodiment depicted in FIGS. 1A-1B, as well as others described herein, the control unit 46 in conjunction with a set of sensors 48 integrated within the housing 14 can control the operation of the ultraviolet treatment on the biological fluids. In operation, the set of sensors 48 can generate signals representative of the conditions that each are configured to detect and send those signals to the control unit 46 which can activate the ultraviolet treatment, specify operating parameters for the treatment, monitor the treatment, adjust the operating parameters according to feedback provided by the sensors, and terminate the treatment after the cleaning.

One type of sensor that can be deployed can include a bacterial fluorescence sensor that can detect the amount or presence of bacteria, germs, viruses, and/or the like, which is present in the biological fluid. In particular, the bacterial fluorescence sensor can generate signals representative of the condition of the biological fluid with respect to the amount of bacteria, germs, viruses, and the like, and sends those signals to the control unit 46. The control unit 46 can determine whether an ultraviolet treatment is necessary as a function of the signals provided by the bacterial fluorescence sensor using any solution. Additionally, the control unit 46 can determine the progress of the treatment depending on the presence of these signals.

In one embodiment, the control unit 46 can activate the operation of the ultraviolet radiation sources 44 in response to determining that the presence of an amount of bacteria, germs, viruses, and/or the like within the biological fluid, which exceeds a predetermined threshold, and thus, necessitating an ultraviolet treatment. Activating the operation of the ultraviolet radiation sources 44 by the control unit 46 can include specifying any of a plurality of the operating parameters. In one embodiment, the plurality of operating parameters can include a wavelength of the ultraviolet radiation emitted from the ultraviolet radiation sources 44, an intensity or dosage of the ultraviolet radiation delivered to the biological fluid by the ultraviolet radiation sources 44, and a treatment time that the ultraviolet radiation sources 44 deliver the ultraviolet radiation to the biological fluid. Other operating parameters can include an angular distribution of the ultraviolet radiation transmitted from the ultraviolet radiation sources 44, a power setting for operating the ultraviolet radiation sources 44, and a maximum operating temperature for the ultraviolet treatment. It is understood that these operating parameters are illustrative of some of the parameters that can be set by the control unit 46 and is not meant to be limiting as other parameters exist which may be specified.

Furthermore, it is understood that the sensors 48 can include a multitude of different types of sensors and that the various embodiments of the present invention are not meant to be limited to a bacterial fluorescence sensor. Other sensors that are suitable for use with the ultraviolet treatment system 10 can include, but are not limited to, a temperature sensor, a chemical sensor, a radiation sensor (e.g., an ultraviolet dose counter or meter), a transparency sensor, etc. Each of these sensors could detect the level or amount of a particular parameter that each is intended to measure and send signals thereof to the control unit 46. For example, a temperature sensor can detect the temperature within the housing 14 and/or the temperature of the surface of the medical device 12, a chemical sensor can detect a level of a particular chemical that is present in the biological fluid, a radiation sensor can detect a level of radiation that is present in the biological fluid, and a transparency sensor can evaluate the transparency of the biological fluid within the medical instrument and enable the control unit 46 to invoke a feedback electrical control module that can determine the intensity levels of the ultraviolet radiation sources based on the transparency of the fluid. These sensors can be deployed along with the ultraviolet radiation sources 44 in any desired configuration. For example, the sensors 48 can be interspersed with the ultraviolet radiation sources 44 or separated from each other.

The control unit 46 can include a timer with switches and/or the like, to manage the duration that the ultraviolet radiation sources 44 are on for a particular ultraviolet treatment and ensure that radiation is applied to the biological fluid for that duration. In one embodiment, the control unit 46 operating in conjunction with the timer can manage the amount of time that the ultraviolet radiation sources 44 radiate in the UV-C range versus the UV-B range. The duration and frequency treatment that the ultraviolet radiation sources 44 are utilized can depend on detected condition signals provided to the control unit 46 by any of the sensors 48, as well as any other predetermined treatment factors such as the length that a particular biological fluid has been in storage, a source of the fluid, and whether a set predefined treatment schedule is being followed.

During operation of an ultraviolet treatment, the control unit 46 can be used to control at least one of a plurality of predetermined ultraviolet radiation characteristics associated with the ultraviolet radiation emitted from the ultraviolet radiation sources 44. The predetermined ultraviolet radiation characteristics that can be controlled by the control unit 46 can include wavelengths, intensities, and durations and/or the like. In one embodiment, the control unit 46 can control the wavelength of ultraviolet radiation and intensity spatially over a surface of the medical device 12 where the biological fluid is being treated. As an example, the control unit 46 can control the ultraviolet radiation sources 44 to operate at a target wavelength and intensity for a duration that is designed for the disinfection of bacteria and/or viruses of the biological fluid.

In an embodiment, the control unit 46 can determine a target intensity for radiation to be directed to the biological fluid. The intensity range can be determined based on attributes of the ultraviolet radiation sources 44. The target intensity can be incremented in steps or continuously over the range of times corresponding to the varying intensities. The range of times can be determined based on, for example, feedback data acquired regarding a severity of contamination typical for a period of time.

In an embodiment, the control unit 46 can generate outputs for presentation to a user that correspond to the ultraviolet treatments. The outputs can be transmitted to a user via a number of different output devices that can include, for example, a vibration device, a visible light (e.g., flashing), an auditory signal generated by a speaker, and/or the like.

In addition, during the operation of the ultraviolet treatment, the control unit 46 can be used to turn on or off the ultraviolet radiation sources 44 dependent upon the detected conditions provided by the sensors 48. In one embodiment, the control unit 46 can turn on or off each of the ultraviolet radiation sources 44 via an actuator. Also, the control unit 46 can be used to adjust one or more of the ultraviolet radiation characteristics based on the conditions detected by the sensors 48. For example, the control unit 46 can use the signals from a bacterial fluorescence sensor that are representative of the amount of bacteria, germs, viruses, and/or the like, present in the biological fluid to adjust the intensity, the wavelength, the duration and or the pattern of the ultraviolet radiation emitted from any of the ultraviolet radiation sources 44. In another embodiment, the control unit 46 can be configured to interrupt the operation of the ultraviolet radiation sources 44 in response to receiving temperature signals from a temperature sensor and determining that the temperature of the ultraviolet treatment has exceeded the maximum temperature. The control unit 46 can resume the ultraviolet treatment after a predetermined cooling time has elapsed.

The control unit 46 can also include a wireless transmitter and receiver that is configured to communicate with a remote location via WiFi, BLUETOOTH, and/or the like. As used herein, a remote location is a location that is apart from the ultraviolet treatment system. For example, a remote computer can be used to transmit operational instructions to the wireless transmitter and receiver. The operational instructions can be used to program functions performed and managed by the control unit 46. In another embodiment, the wireless transmitter and receiver can transmit ultraviolet treatment results, data from the 48 to the remote computer, to facilitate maintenance and diagnostic operations on the ultraviolet cleaning treatment system.

The control unit 46 can include an input component and an output component to allow a user to interact with the ultraviolet treatment system 10 and the control unit 46, and to receive information therefrom. In one embodiment, the input component can permit a user to adjust at least one of the aforementioned plurality of operating parameters. This can include making adjustments during the ultraviolet treatment operation and/or prior to initiating a treatment. In one embodiment, the input component can include a set of buttons and/or a touch screen to enable a user to specify various input selections regarding the operating parameters as well as the ultraviolet treatment. In one embodiment, the output component can include a visual display for providing status information on the ultraviolet treatment (e.g., time remaining, the presence of bacteria, viruses, germs or the like), an indication that a ultraviolet treatment is recommended, an indication that the biological fluid has been sterilized, disinfected, sanitized, a simple visual indicator that displays whether a ultraviolet treatment is underway (e.g., an illuminated light) or if the treatment is over (e.g., absence of an illuminated light).

The ultraviolet treatment system 10 can further include a power source that is configured to power each of the ultraviolet radiation sources 44, the control unit 46 and the sensors 48. In one embodiment, the power source can take the form of one or more batteries, a vibration power generator that can generate power based on magnetic inducted oscillations or stresses developed on a piezoelectric crystal. In another embodiment, the power source can include a super capacitor that is rechargeable. Other power components that are suitable for use as the power source for the ultraviolet treatment system 10 and the control unit 46 can include a mechanical energy to electrical energy converter such as a piezoelectric crystal, and a rechargeable device.

The ultraviolet treatment system 10 can also include a heat dissipating component. A heat dissipating component enables the electronic componentry associated with the ultraviolet radiation sources 44, the control unit 46, the sensors 48 and power source to operate efficiently without overheating. Examples of a heat dissipating component can include, but are not limited to, a heat sink, an air fan, and/or other heat dissipating mechanisms, such as liquid heating.

Figure 12:
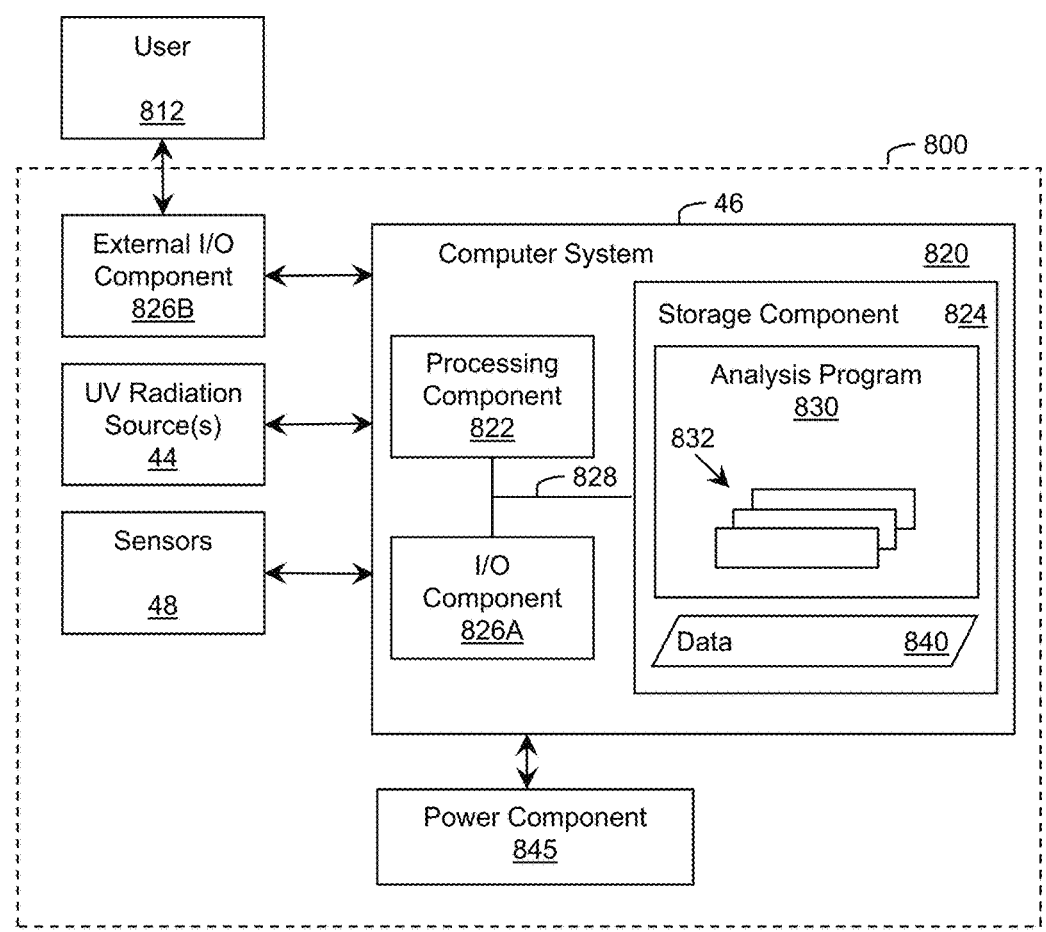
FIG. 12 shows a schematic block diagram representative of an overall processing architecture of an ultraviolet treatment system that is applicable to any of the systems describe herein according to an embodiment.
Figure 13:
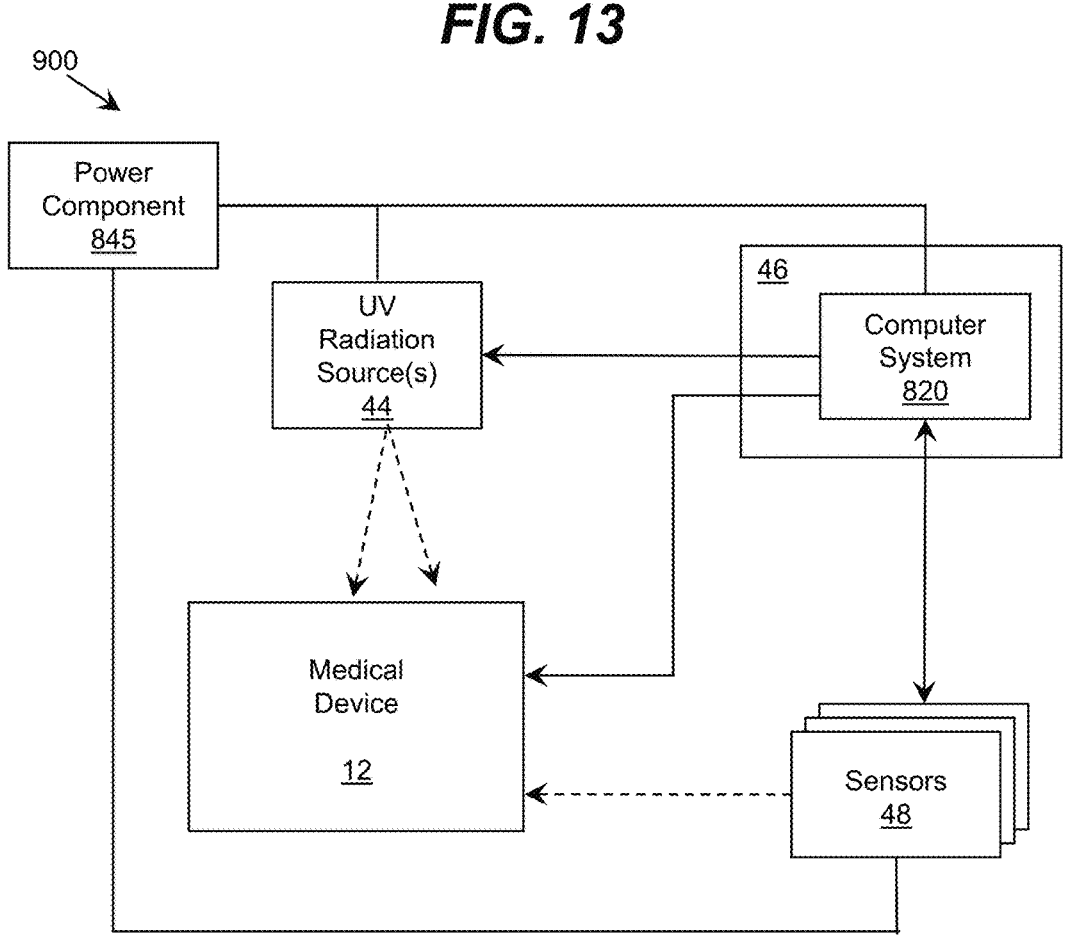
FIG. 13 shows a schematic of an illustrative environment in which the architecture of the ultraviolet treatment system depicted in FIG. 12 can be used to facilitate an ultraviolet treatment of a biological fluid according to an embodiment.

The aforementioned components of the ultraviolet cleaning treatment system are illustrated in FIGS. 12-13 and discussed further with regard to these figures. These components of the ultraviolet cleaning treatment system are suitable for use with the various other ultraviolet treatment systems described herein. It is understood that the functions of these components can vary and will depend on the type of biological fluid and the medical instrument in which the fluid is used with. Thus, the functions described are only illustrative of examples of particular functions and operations to be performed and are not meant to be limiting to the embodiment of FIGS. 1A-1B as well as to the ultraviolet treatment systems used in conjunction with the other embodiments described herein.

Figure 2:
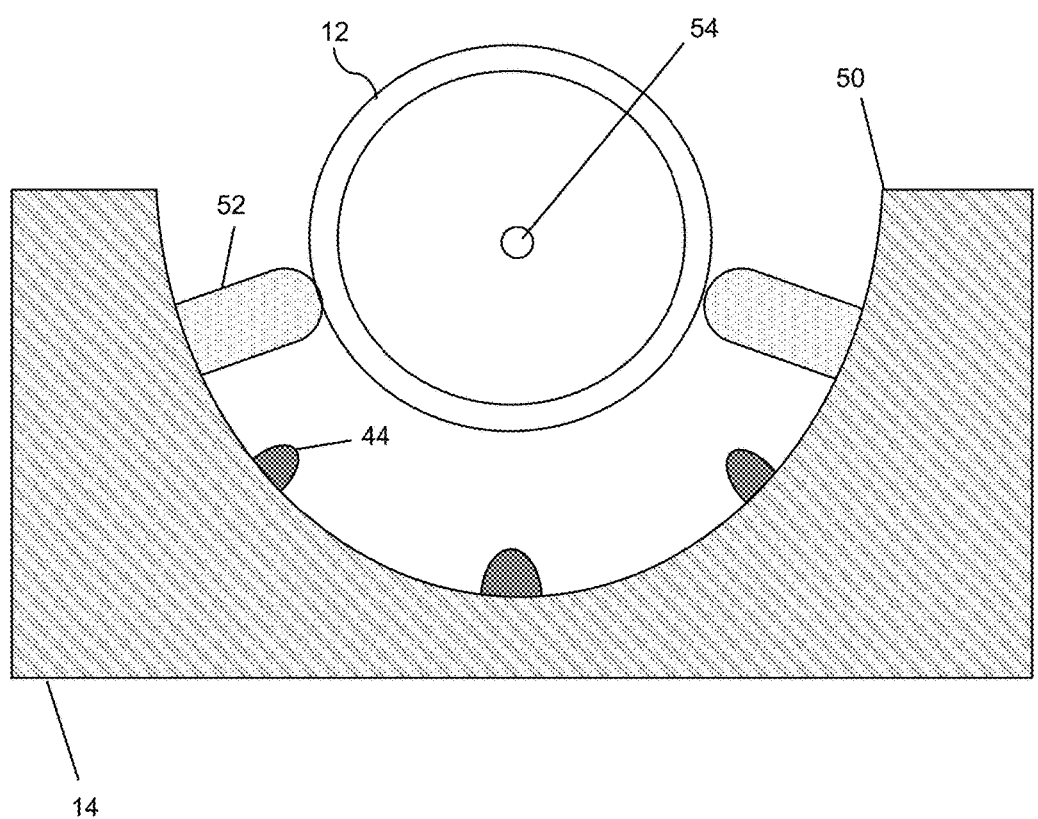
FIG. 2 shows a schematic cross-sectional view of an illustrative housing depicted in FIGS. 1A-1B with an optical element used in conjunction with at least one ultraviolet radiation source according to an embodiment.

FIG. 2 shows a schematic cross-sectional view of the housing 14 depicted in FIGS. 1A-1B with an optical element 50 used in conjunction with at least one ultraviolet radiation source 44 according to an embodiment. In particular, the optical element 50 can be used to focus ultraviolet radiation emitted from the ultraviolet radiation sources 44 to the medical instrument 12 and the biological fluid therein. In this embodiment and others described herein, the optical element 50 can be integrated within the housing 14 to direct and redirect ultraviolet radiation emitted from the UV LED source(s) toward the medical instrument 12 and the biological fluid. In the embodiment depicted in FIG. 2, the optical element 50 can include a parabolic mirror element formed on an inner surface of the housing 14 along with the ultraviolet radiation sources 44 arranged on the parabolic mirror element. As shown in FIG. 2, the inner surface of the housing 14 can include one or more support elements 52 (e.g., plastic or rubber extensions) that extend outward from the inner surface, which support the medical instrument and prevent contact with the ultraviolet radiation sources 44 and the parabolic mirror element. In this manner, the ultraviolet radiation sources can emit ultraviolet radiation to a focus point 54 centered in the medical instrument 12 and the parabolic mirror element can direct and redirect the radiation towards the focus point to effectuate an ultraviolet treatment of the biological fluid in the instrument. In one embodiment, the support elements 52 can be coated with an ultraviolet reflective material to provide additional recycling of the ultraviolet radiation. In addition, the parabolic mirror element can include an ultraviolet reflective material such as for example, polished aluminum, in order to provide further recycling of the ultraviolet radiation.

Although a parabolic mirror element is mentioned as one type of optical element that can be used, it is understood that other types of optical elements can be utilized with the housing 14 as well as the housings of the other embodiments described herein, to deliver sufficient dosage of ultraviolet radiation to particular section(s) of the medical instrument 12 to effectuate an ultraviolet treatment of biological fluid at these section(s). For example, an omnidirectional mirror and a planar mirror with multiple dielectrics and at least one metallic layer can be formed on an inner surface of the housing. Other examples of optical elements that can be deployed in the housing can include lenses, prismatic ultraviolet transparent elements, and/or the like. In another embodiment, a wave guiding layer can be formed on an inner surface of the housing to deliver light to a particular section of the medical instrument.

Figure 3:
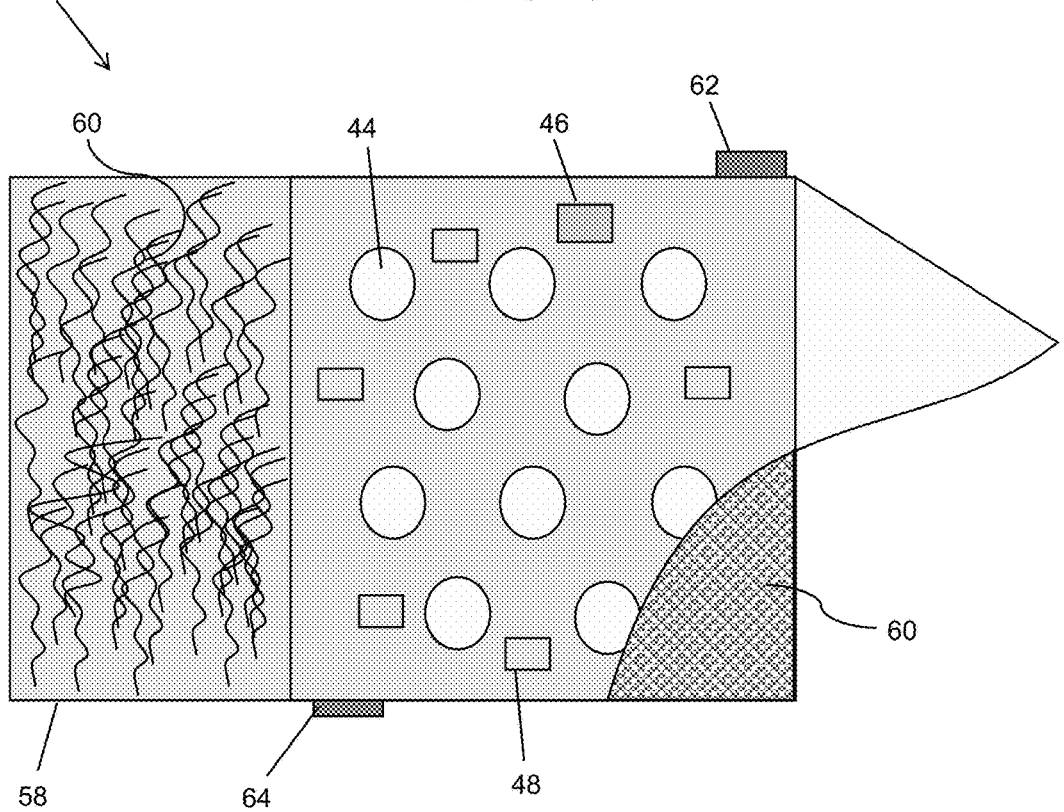
FIG. 3 shows schematic top view of an illustrative ultraviolet treatment system for treating a biological fluid in a medical instrument with a housing in the form of a flexible sleeve according to an embodiment.

FIG. 3 shows a schematic top view of an ultraviolet treatment system 56 for treating a biological fluid in a medical instrument according to an embodiment. In this embodiment, the ultraviolet treatment system 56 includes a housing 58 in the form of a flexible sleeve that is configured to wrap around the medical instrument. The housing 58 can have a fastener closure 60 to secure the housing to the medical instrument after wrapped there around. In one embodiment, the fastener enclosure 60 can include a hook and loop fastener that couples one end of the sleeve to another end. In this manner, the ultraviolet radiation sources 44 and the other components of the ultraviolet treatment system 56 such as the control unit 46 and the sensors 48 can be arranged in an internal portion of the sleeve between the fastener closure 60.

As shown in FIG. 3, the ultraviolet treatment system 56 can also include other components to facilitate the ultraviolet treatment of the biological fluid. For example, the ultraviolet treatment system 56 can include a power source 62 to power the ultraviolet radiation sources 44, the control unit 46, the sensors 48 and any other components like those mentioned above that can be used to effectuate an ultraviolet treatment of the biological fluid. In one embodiment, the power source can include rechargeable batteries or non-rechargeable batteries. It is understood that any of the other aforementioned examples of power sources can be utilized with the ultraviolet treatment system 56. FIG. 3 shows that the ultraviolet treatment system 56 can also include a data port 64 that can communicate with an external device. For example, the data port 64 can enable the control unit 46 to communicate with a remote computing device. In this manner, information compiled by the control unit 46 such as for example, values for the operating parameters, status information, etc., can be transmitted to the remote computing device. Similarly, the data port 64 can convey information from the remote computing device to the control unit 46 such as for example, programming instructions, software updates, etc.

Figure 4:
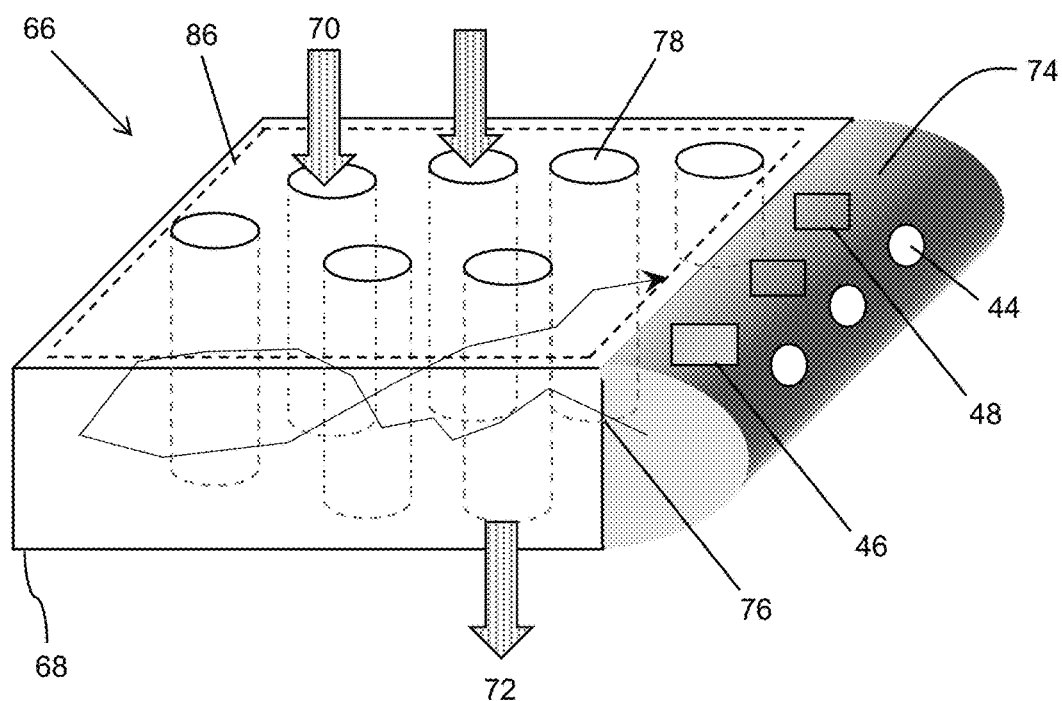
FIG. 4 shows a schematic perspective view of an illustrative pre-treatment component according to an embodiment that is configured to treat a biological fluid prior to receiving a treatment from an ultraviolet treatment system described herein.

FIG. 4 shows a schematic perspective view of a pre-treatment device component 66 according to an embodiment that is configured to treat a biological fluid prior to receiving a treatment from an ultraviolet treatment system such as any of those described herein. The pre-treatment component 66 can include an ultraviolet transparent enclosure 68 having an inlet port 70 and an outlet port 72 for transporting the biological fluid there through, that is within an ultraviolet impenetrable housing (not illustrated for clarity). The pre-treatment component 66 can further include at least one pre-treatment ultraviolet radiation source 44 located about the ultraviolet transparent enclosure 68 to pre-treat the biological fluid with ultraviolet radiation. A set of sensors 48, such as any of those previously mentioned, can be arranged along with the ultraviolet radiation sources 44. The ultraviolet radiation sensors 44 and the sensors 48 can operate in conjunction with the control unit 46 to effectuate a pre-ultraviolet treatment of the biological fluid passing through the ultraviolet transparent enclosure 68 in a manner similar to the ultraviolet treatment described herein.

In one embodiment, the ultraviolet transparent enclosure 68 can include a porous ultraviolet transparent element having an ultraviolet transparent material. Examples of a porous ultraviolet transparent element having an ultraviolet transparent material can include an ultraviolet transparent fluoropolymer chosen from the group consisting of EFEP, ETFEP, Teflon®, and FEP.

The ultraviolet transparent enclosure 68 can include portions or sections that contain ultraviolet reflective material to recycle the ultraviolet radiation emitted from the ultraviolet radiation sources 44. Any of the aforementioned ultraviolet reflective material is suitable for use with the ultraviolet transparent enclosure 68.

Additionally, the ultraviolet transparent enclosure 68 can have optical elements arranged with ultraviolet radiation sources 44. In one embodiment, the section of the ultraviolet transparent enclosure 68 containing the ultraviolet radiation sources 44 can include optical elements such as any of the previously mentioned optical elements. In one embodiment, the ultraviolet transparent enclosure 68 can include an ultraviolet reflector 74 integrated with the ultraviolet radiation sources 44 to facilitate delivery of the ultraviolet radiation emitted from the sources into the ultraviolet transparent enclosure 68. The delivery and path of the light from the ultraviolet radiation generated from the ultraviolet radiation sources is depicted in FIG. 4 by the light ray 76. It is understood, that the location and arrangement of the ultraviolet radiation sources 44 in the ultraviolet transparent enclosure 68 is not limited to one particular side of the enclosure as illustrated in FIG. 4. On the other hand, the ultraviolet radiation sources can be disposed at opposing sides of the ultraviolet transparent enclosure, and even all sides of the enclosure.

In one embodiment, the ultraviolet transparent enclosure 68 can include a plurality of pre-treatment channels 78 that transport the biological fluid from the inlet port 70 to the outlet port 72. Microchannels is one example of channels that can be deployed as the pre-treatment channels 78. In order to properly treat the biological fluid within the ultraviolet transparent enclosure 68, the microchannels should have a diameter comparable to a light attenuation length scale for the light having a target wavelength to effectuate a treatment of the biological fluid. As used herein, the light attenuation length scale or light absorption optical distance is the distance that light passes within a biological fluid before its intensity is decreased by at least a factor of $\exp(1) \approx 2.718$. In one embodiment, the diameter of the microchannels can be selected to be less than the light attenuation length scale (light absorption optical path). In another embodiment, the diameter of the microchannels is comparable to the ultraviolet light absorption wavelength. Microchannels with these characteristics facilitate near homogeneous irradiation levels throughout the channels. Furthermore, microchannels with these characteristics make the ultraviolet transparent enclosure 68 well suited for use with ultraviolet absorbing biological liquids such as for example, urine, blood or milk.

The pre-treatment channels 78 can be formed from an ultraviolet transparent material. In one embodiment, the ultraviolet transparent material can include an ultraviolet transparent fluoropolymer. Examples of an ultraviolet transparent fluoropolymer material can include, but are not limited to, fluorinated ethylene propylene co-polymer (EFEP), fluorinated ethylene propylene (FEP), polytetrafluoroethylene (PTFE), ethylene chlorotrifluoroethylene (ECTFE), polychlorotrifluoroethylene (PCTFE), perfluoroalkoxy (PFA), polyvinylidene fluoride (PVDF), ethylene tetrafluoroethylene (ETFE), tetrafluoroethylene hexafluoropropylene vinylidene fluoride co-polymer (THV), low density polyethylene (LDPE), perfluoro methyl alkoxy (MFA), and/or the like. While primarily described in conjunction with fluoropolymers, it is understood that other comparable materials can be utilized such as polylactide (PLA), fused silica, sapphire, THE, and/or the like. In one embodiment, a pre-treatment channel formed from EFEP can be obtained through the imprinting technology.

Figure 5:
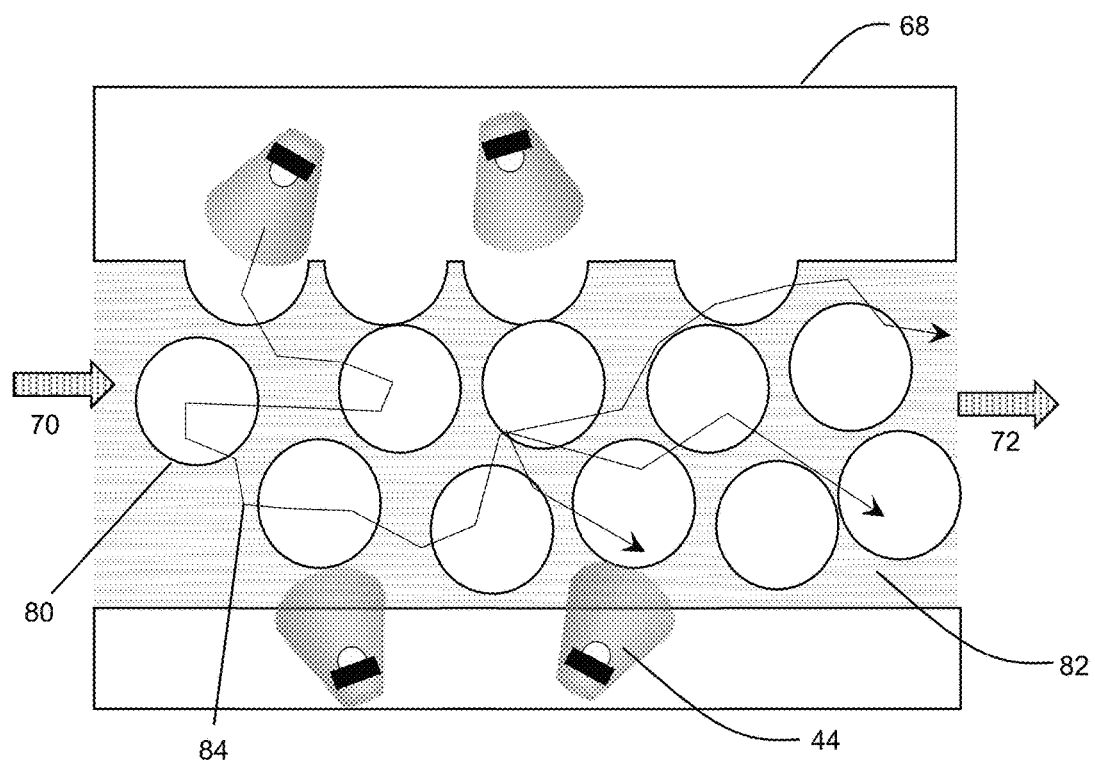
FIG. 5 shows a schematic cross-sectional view of an illustrative pre-treatment component having ultraviolet transparent domains placed in a fluid stream between at least one ultraviolet radiation source to pre-treat a biological fluid according to an embodiment.

In another embodiment, as shown in FIG. 5, the ultraviolet transparent enclosure 68 of FIG. 4 can include a plurality of domains 80 that can include ultraviolet reflective domains or ultraviolet transparent domains located between the inlet port 70 and the outlet port 72 to provide a porous ultraviolet transparent media capable of producing motion to the light rays of the emitted radiation. As used herein, an ultraviolet reflective domain is any object that has a surface reflectivity of at least 40% to the target ultraviolet radiation directed normal to the surface, while an ultraviolet transparent domain is any object that has at least 20% of ultraviolet light penetrating through the widest cross section of the domain. In one embodiment, the ultraviolet reflective/transparent domains 80 can be located between the ultraviolet radiation sources 44 in the stream path 82 of the biological fluid. It is understood that the particular ultraviolet reflective domain and ultraviolet transparent domain materials can be selected to be biologically and chemically inactive when placed within the biological fluid. In an embodiment, such materials can comprise fluoropolymers, $SiO_2$, anodized aluminum oxide (AAO), and/or the like.

In one embodiment, the ultraviolet transparent domains 80 can include light guiding elements such as for example, ultraviolet transparent fluoropolymers, fused silica, AAO membranes, sapphire and/or the like. In one embodiment, the ultraviolet transparent domains can take the form of fused silica balls, fluoropolymer balls or other ball like domains made from ultraviolet transparent material.

In one embodiment, the ultraviolet reflective domains 80 can comprise balls of polished aluminum. Alternatively, the ultraviolet reflective domains 80 can comprise PTFE. In another embodiment, the ultraviolet reflective domains can comprise glass particles covered by ultraviolet reflective film such as Teflon®, aluminum film and/or GORE® material. In still another embodiment, the ultraviolet reflective domains can comprise a set of dielectric films forming a Bragg mirror or an omnidirectional mirror. For instance, the omnidirectional mirror can comprise evaporated aluminum with a top most film being $Al_2O_3$.

It is understood that embodiments in which an ultraviolet treatment system use the channels, the ultraviolet reflective domains, the ultraviolet transparent domains, or other elements that can transport the biological fluid, can utilize additional modalities to facilitate disinfection, sterilization and sanitation of the fluid in addition to the ultraviolet radiation sources 44. For example, some of the surfaces of the channels, the ultraviolet reflective domains, or the ultraviolet transparent domains can include photo-catalysts designed to improve the treatment of the biological fluid. In one embodiment, a photo-catalyst such as for example, $TiO_2$ can be applied to the surfaces of the channels, the ultraviolet reflective domains, or the ultraviolet transparent domains.

In one embodiment, the ultraviolet radiation sources 44 can be arranged in portions or sections of the ultraviolet transparent enclosure 68 that are ultraviolet transparent. For example, as shown in FIG. 5, the ultraviolet radiation sources 44 can be arranged in opposing side portions of the enclosure 68 between the stream path 82 for the biological fluid. In this manner, the ultraviolet radiation sources 44 can emit the ultraviolet radiation and the ultraviolet reflective domains 80 can redirect the optical path of the light 84 emitted from the sources to attain a fuller treatment of the biological fluid. It is understood that the ultraviolet radiation sources 44 can be separate, without the need to be embedded into an ultraviolet transparent material. In addition, it is understood that the stream path 82 of the biological fluid can be from a top end to a bottom end of the ultraviolet transparent 68 and is not limited to the left to right flow direction depicted in FIG. 5.

Referring back to FIG. 4, the ultraviolet transparent enclosure 68 of the pre-treatment component can include a filtering element 86 that removes undesired contaminants from the biological fluid. Examples of a filtering material that is suitable for use as the filtering element 86 can include, but is not limited to, AAO, porous silicon oxide, carbon and various phases of carbon, and/or the like.

Figure 6A:
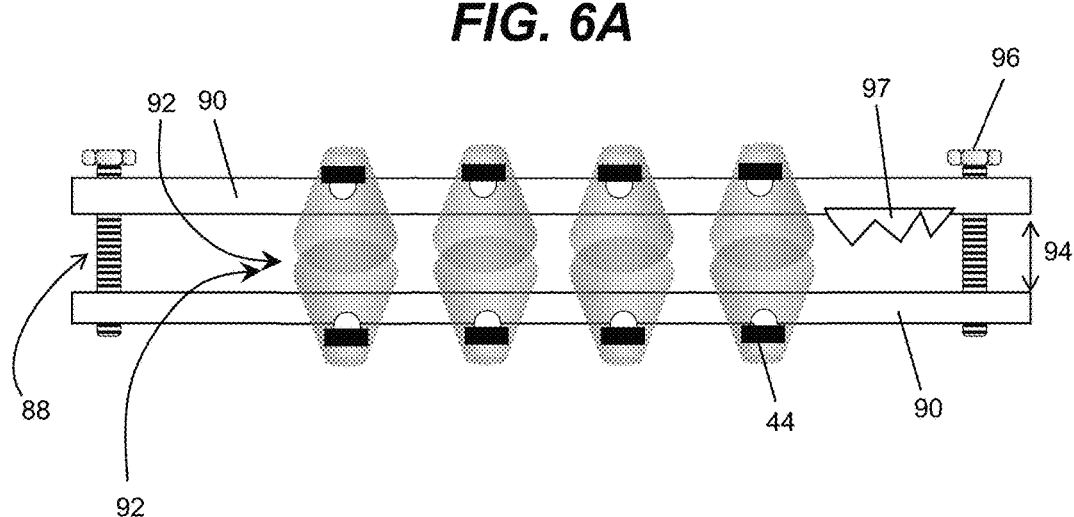
FIG. 6A-6B show schematic views of an illustrative pre-treatment channel that can be used in a pre-treatment component to transport the biological fluid from the outlet port to the inlet port according to an embodiment.
Figure 6B:
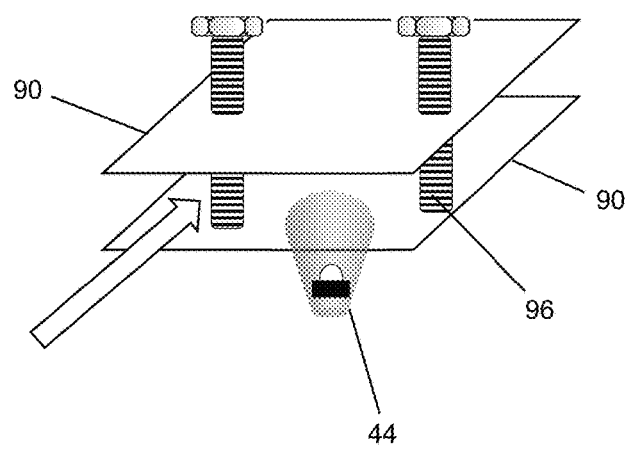

FIGS. 6A-6B show schematic views of a pre-treatment channel 88 according to an embodiment that can be used to transport a biological fluid from an inlet port to an outlet port in a pre-treatment component; for example, the pre-treatment component 68 depicted in FIG. 5. In the embodiment illustrated in FIGS. 6A-6B, the pre-treatment channel 88 can be formed by plates 90. The plates 90 can include either ultraviolet reflective layers or ultraviolet light guiding layers. Examples of ultraviolet reflective layers suitable for use as the plates 90 can include, but are not limited to, polished aluminum, Bragg reflective dielectric mirrors, omni-directional mirrors comprising dielectric and metallic layers (e.g., aluminum), and/or the like. Examples of ultraviolet light guiding layers suitable for use as the plates 90 can include, but are not limited to, $SiO_2$, $Al_2O_3$, $CaF_2$, $MgF_2$, fluoropolymers, UV transparent cavities filled with UV transparent fluids such as water, and/or the like.

The ultraviolet radiation sources 44 used in an ultraviolet treatment in which pre-treatment channels would be deployed, can be incorporated in the plates 90 as shown in FIGS. 6A-6B. In this manner, the plates 90 can guide the light emitted from the ultraviolet radiation sources to different portions of the flow path 92 for the biological fluid. In one embodiment, the operating parameters of the ultraviolet radiation sources 44 can be specified to attain maximum efficiency in radiating the biological fluid. In addition, orienting the manner in which the light of the ultraviolet radiation is generated from the ultraviolet radiation sources 44 can also facilitate maximum efficiency in radiating the biological fluid. For example, in some configurations, the light generated from the ultraviolet radiation sources 44 can be oriented at an angle to the normal of the plates 90 to provide additional light guiding.

It is understood that other modalities can be employed to improve the efficiency in radiating the biological fluid passing through pre-treatment channels 88 like the ones depicted in FIGS. 6A-6B. For example, the plates 90 can include roughness elements 97 either through the entire surface area adjacent to the pre-treatment channel 88 or to a portion of the surface area adjacent to the channel. In another embodiment, the surfaces of the plates 90 adjacent to the pre-treatment channel 88 can be partially transparent and partially reflective. The exact transparency and reflectivity values for such an implementation would be variable in order to attain best light guiding and recycling of the ultraviolet light.

Having the ultraviolet radiation sources 44 incorporated in the plates 90 in the manner depicted in FIGS. 6A-6B make this configuration for use as an ultraviolet illuminator that can be deployed within an ultraviolet treatment system. U.S. patent application Ser. No. 14/478,266 filed on 5 Sep. 2014, entitled "ULTRAVIOLET DIFFUSIVE ILLUMINATION", now U.S. Pat. No. 9,550,004, which is incorporated herein by reference, provides further details of an ultraviolet illuminator, of which its implementation in an overall system could be applied with this embodiment to provide ultraviolet diffusive illumination of a biological fluid.

In one embodiment, a width 94 of the plates 90 used to form the pre-treatment channels 88 can be adjusted to expand or decrease the focus of the irradiation through a particular channel. This feature allows adjusting the height of the channel for efficient irradiation depending on the absorption properties of the biological fluids. For example, for highly absorbing fluids, the channel height is decreased allowing for thorough radiation of the fluid. A mechanical fastener can be used to expand or decrease the width 94 of the pre-treatment channels 88. In one embodiment, as shown in FIGS. 6A-6B, the mechanical fastener can include a screw 96 or other similar fastening devices. It is understood that other mechanical mechanisms can be used to control the width 94 of the pre-treatment channel 88. For example, the pre-treatment channels 88 can be separated by a spring element, such that the width 94 between the channels can be obtained by applying an external pressure to the plates 90 that creates a force balance between an external force and a restoring force of the spring elements separating the channels. In one embodiment, the external force can be applied by an inflation element, that through inflation applies the force on the plates 90. Additional inflation elements can be also inserted between the plates 90 to obtain the desired external force.

Figure 7:
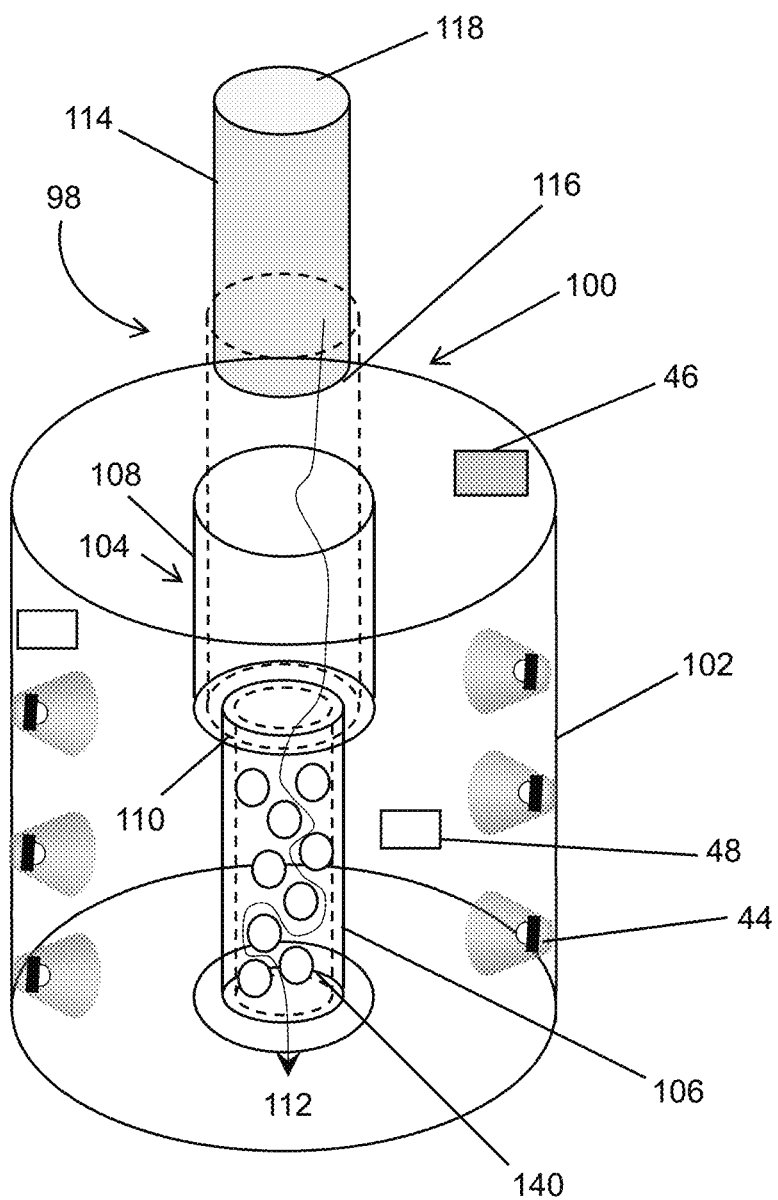
FIG. 7 shows a schematic view of an illustrative housing having an outer chamber and an inner chamber that can be used with an ultraviolet treatment system according to an embodiment.

FIG. 7 shows a schematic view of an ultraviolet treatment system 98 that can be used to treat a biological fluid in a medical instrument such as for example, a catheter, according to an embodiment. As shown in FIG. 7, the ultraviolet treatment system 98 can include an ultraviolet impenetrable housing 100 configured to enclose a portion of a medical instrument (not illustrated) containing a biological fluid. The housing 100, which can take the form of a cylindrical shape, can include an outer chamber 102 and an inner chamber 104 enclosed by the outer chamber, both of which can be cylindrically-shape, such that the outer chamber 102 is a wider cylinder that surrounds a narrower inner cylinder of the inner chamber 104. In one embodiment, the inner chamber 104 can include a first inner chamber 106 and a second inner chamber 108 surrounding the first inner chamber, such that the first inner chamber has an inflow connection 110 and an outflow connection 112 with the biological fluid.

The ultraviolet treatment system 98 can further include at least one ultraviolet radiation source 44 integrated within the housing 100 that is configured to emit ultraviolet radiation towards the biological fluid that enters the housing from the medical instrument. In one embodiment, the ultraviolet radiation sources 44 can be located on an outer wall of the outer chamber 102 within the outermost layer of the housing 100 that is impenetrable to ultraviolet light (e.g., ultraviolet absorbing material), and oriented to emit ultraviolet radiation to the inner chamber 104. The ultraviolet radiation sources 44 can also be located on an inner wall of the outer chamber. In addition, the ultraviolet treatment system 98 can include a set of the sensors 48 to obtain a variety of measurements before, during and after the ultraviolet treatment of the biological fluid. In one embodiment, the sensors 48 can be arranged on the outer or inner wall of the outer chamber 102 of the housing 100 along with the set of ultraviolet radiation sources 44. The control unit 46 can control the ultraviolet radiation sources 44 and the sensors 48 in the manner described above to effectuate an ultraviolet treatment of the biological fluid. It is understood that the embodiment depicted in FIG. 7 represents only one possible configuration for the ultraviolet radiation sources 44, the control unit 46 and the sensors 48 and is not meant to limit the scope of this embodiment.

In one embodiment, the outer chamber 102 of the housing 100 can have inner walls that include ultraviolet reflective properties. In this manner, the inner walls of the outer chamber 102 can recycle or recirculate the ultraviolet radiation emitted from the ultraviolet radiation sources 44. Examples of materials that can be applied as layers, films or coatings to the inner walls of the outer chamber 102 of the housing 100 can include, but are not limited to, polished aluminum, GORE®, PTFE and other fluoropolymers.

In another embodiment, the inner walls of the outer chamber 102 can include optical elements to focus the ultraviolet radiation emitted from the ultraviolet radiation sources 44 to the inner chamber 104 of the housing 100 in which the biological fluid flows there through. An example of an optical element that can be arranged with the inner walls of the outer chamber 102 can include, but are not limited to, a parabolic mirror element (e.g., a parabolic reflector). Other examples can include an omnidirectional mirror, a planar mirror, lenses, prismatic ultraviolet transparent elements, a wave guiding layer, etc.

In one embodiment, the inner chamber 104 can include an ultraviolet transparent chamber, with its walls formed from ultraviolet transparent material. Examples of ultraviolet transparent material that is suitable for use with the walls of the inner chamber 104, including the alternative embodiment in which the inner chamber includes a first inner chamber 106 and a second inner chamber 108, can include, but is not limited to, ultraviolet transparent fluoropolymers, sapphire, $SiO_2$ and/or the like.

FIG. 7 shows that the ultraviolet treatment system 98 can further include a medical instrument connector 114 configured for coupling the inner chamber 104 with the medical instrument in order to permit a flow of biological fluid from the instrument to the housing 100 for irradiation by the ultraviolet radiation sources 44. In one embodiment, the medical instrument connector 114 can include a cylindrical element having a first end 116 that couples to the inner chamber 104 and a second end 118 that couples to the medical instrument. In one embodiment, in which the inner chamber 104 includes a first inner chamber 106 and a second inner chamber 108, the medical instrument connector 114 can mate with both chambers in order to permit the flow of the biological fluid from the medical instrument through the housing 100 via the inflow connection 110 and the outflow connection 112. In one embodiment, as shown in FIG. 9, gaskets 120 such as for example, rubber rings, can be used to support and secure the coupling of the medical instrument connector 114 with the inner chamber 104.

Figure 9:
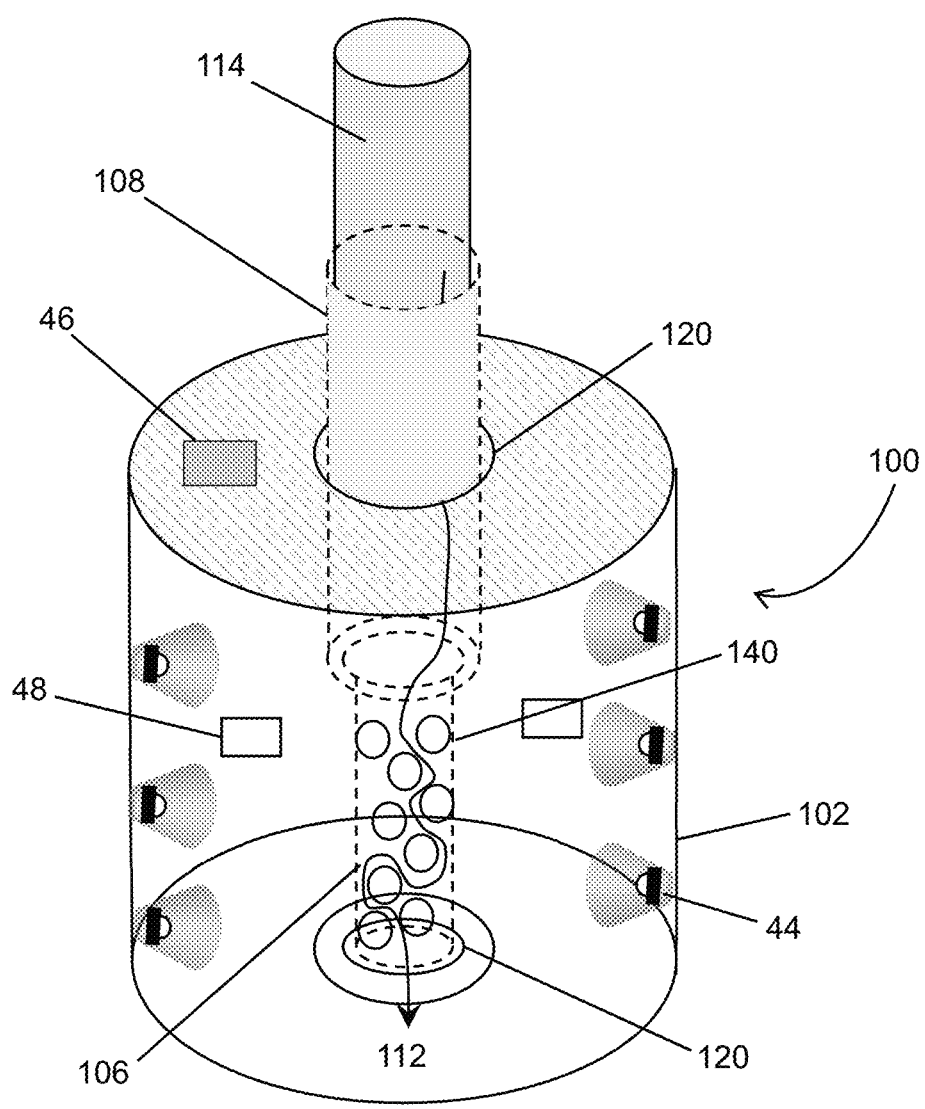
FIG. 9 shows a schematic view of an illustrative housing having an outer chamber and an inner chamber with a medical connector configured for coupling to the inner chamber at one end and a medical instrument at another end according to an embodiment.
Figure 10:
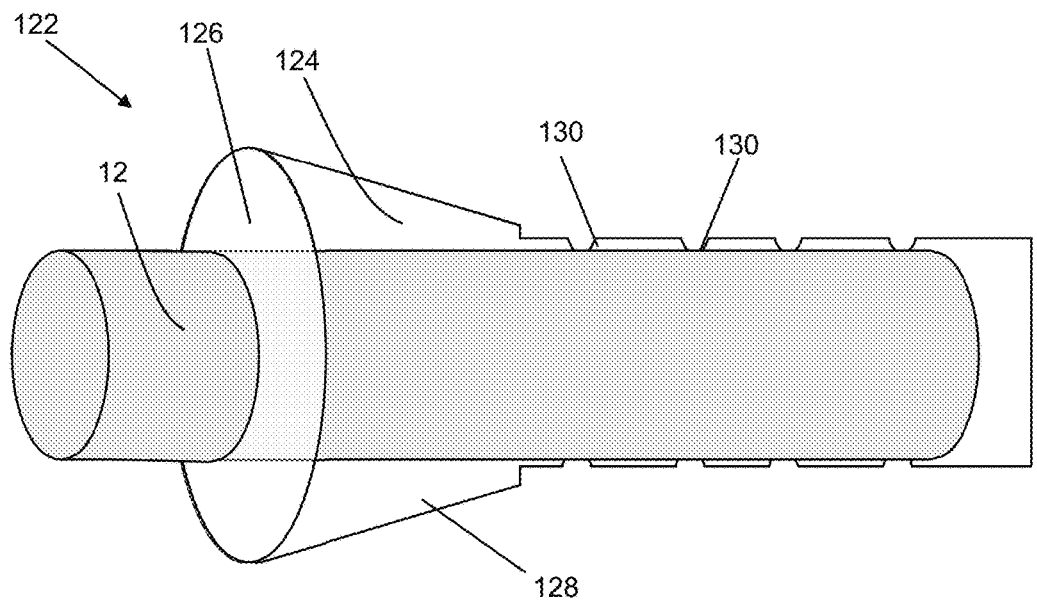
FIG. 10 shows a schematic view of an illustrative medical connector according to another embodiment.

FIG. 10 shows a schematic view of a medical connector 122 according to an embodiment that can be used to couple the inner chamber 104 of the housing of FIGS. 7 and 9 with the medical instrument 12, in order to permit a flow of biological fluid from the instrument to the housing 100 for irradiation by the ultraviolet radiation sources 44. As shown in FIG. 10, the medical connector 122 can include a tapered opening 124, wherein a portion of the opening 126 that receives the medical instrument 12 is wider than a portion of the opening 128 that tapers towards the inner chamber. The tapering (or widening) of the inflow connection of the medical connector 122 allows the ease of insertion of the medical instrument 12. In addition, the medical connector 122 can have friction holding bumps 130 to form a tight connection with the medical instrument 12 upon insertion in the connector.

Figure 11:
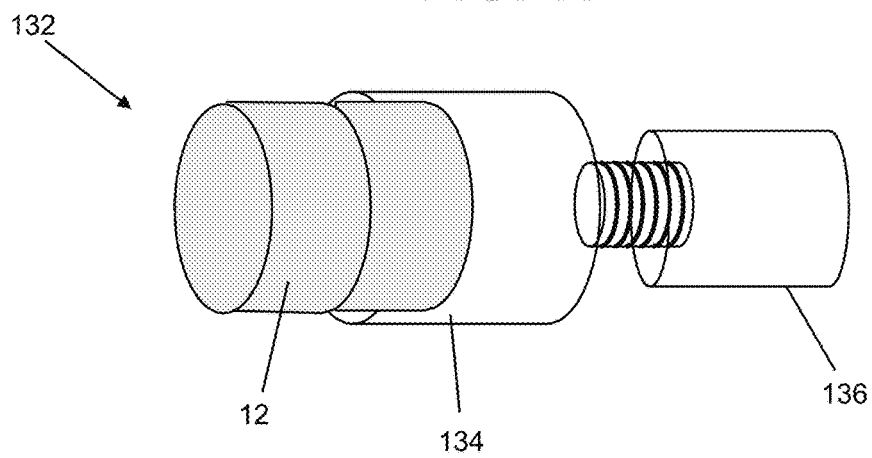
FIG. 11 shows a schematic view of an illustrative medical connector according to still another embodiment.

FIG. 11 shows a schematic view of a medical connector 132 according to another embodiment. In this embodiment, the medical connector 132 can include a first cylindrical enclosure 134 that is threaded to receive a second cylindrical enclosure 136. With this configuration, the medical instrument can be fitted to one end of the first cylindrical enclosure 134, while an opposite end is coupled to the second cylindrical enclosure 136. The unthreaded end of the second cylindrical enclosure 136 can be coupled to the inner chamber 104 of the housing. In this manner, a tight connection can be formed between the medical instrument 12 and the housing of the ultraviolet treatment system.

Figure 8A:
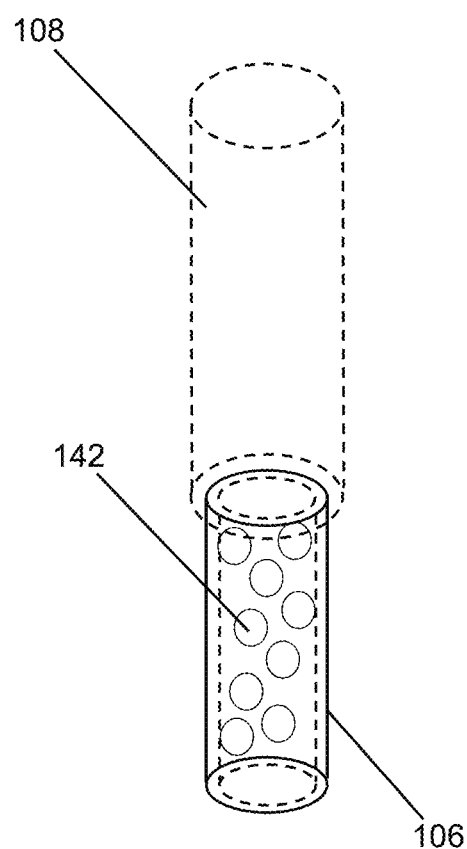
FIGS. 8A-8B show schematic views of the inner chamber depicted in FIG. 7 with ultraviolet reflective domains and channels, respectively, according to an embodiment.
Figure 8B:
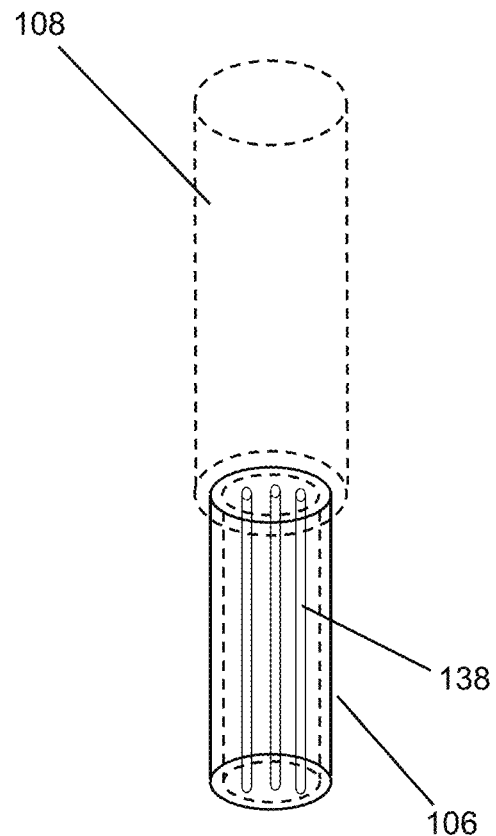

Turning back to FIG. 7 with further reference to FIGS. 8A-8B, the housing 100 of the ultraviolet treatment system 98 can include any of the aforementioned elements that can further improve the irradiation of the biological fluid in a particular flow path such as the one encompassing the inflow connection 110 to the outflow connection 112 within the inner chamber 104. For example, as shown in FIG. 8B, the first inner chamber 106 of the inner chamber 104 can include a plurality of channels 138 to transport the biological fluid from the inflow connection 110 to the outflow connection 112. In one embodiment, the plurality of channels 138 can have scales larger than a millimeter, be as small as a few microns, or in some cases be nano-sized channels. Channels of these sizes can be fabricated utilizing a well-known AAO based fabrication method for porous elements. In one embodiment, the plurality of channels 138 can be fabricated such that the characteristic diameter of the channel is equal to or less than the light absorption optical distance of the target radiation within the biological fluid to be treated.

Instead of channels, the inner chamber 104 of the housing 100 can include either a plurality of ultraviolet reflective domains or ultraviolet transparent domains. For example, in one embodiment, the first inner chamber 106 of the inner chamber 104 can include the ultraviolet reflective domains or the ultraviolet transparent domains. FIG. 7 shows ultraviolet reflective domains 140 in the first inner chamber 106, while FIG. 8A shows ultraviolet transparent domains 142 in the first inner chamber 106. It is understood that any of the aforementioned ultraviolet reflective domains and ultraviolet transparent domains are suitable for use with the ultraviolet reflective domains 140 and the ultraviolet transparent domains 142.

Referring now to FIG. 12, there is a schematic block diagram representative of an overall processing architecture of an ultraviolet treatment system 800 that is applicable to any of the systems describe herein according to an embodiment. In this embodiment, the architecture 800 is shown including the ultraviolet radiation sources 44 (UV radiation source(s)) and the sensors 48 for the purposes of illustrating the interaction of all of the components that are used to provide an ultraviolet treatment of a biological fluid in a particular medical device, instrument or equipment.

As depicted in FIG. 12 and described herein, the ultraviolet cleaning treatment system 800 can include a control unit 46. In one embodiment, the control unit 46 can be implemented as a computer system 820 including an analysis program 830, which makes the computer system 820 operable to manage the ultraviolet radiation sources 44 and the sensors 48 in the manner described herein. In particular, the analysis program 830 can enable the computer system 820 to operate the ultraviolet radiation sources 44 to generate and direct ultraviolet radiation towards a surface of a medical device containing biological fluid and process data corresponding to one or more attributes regarding the device and the fluid, which can be acquired by the sensors 48, and/or an ultraviolet radiation history stored as medical device data 840. The computer system 820 can individually control each ultraviolet radiation source 44 and sensor 48 and/or control two or more of the ultraviolet radiation sources and the sensors as a group. Furthermore, the ultraviolet radiation sources 44 can emit ultraviolet radiation of substantially the same wavelength or of multiple distinct wavelengths.

In an embodiment, during an initial period of operation, the computer system 820 can acquire data from at least one of the sensors 48 regarding one or more attributes of the device and generate data 840 for further processing. The data 840 can include information regarding a presence of biological activity (e.g., microorganisms, viruses, bacteria, and/or the like) in the biological fluid, an amount of radiation (e.g., ultraviolet, infrared, visible, and/or microwave) detected, and/or the like. The computer system 820 can use the data 840 to control one or more aspects of the ultraviolet radiation generated by the ultraviolet radiation source(s) 44 during an ultraviolet treatment of the biological fluid.

Furthermore, one or more aspects of the operation of the ultraviolet radiation sources 44 can be controlled or adjusted by a user 812 via an external interface I/O component 826B.

The external interface I/O component 826B can be located on the exterior of any of the aforementioned medical device illuminators, and used to allow the user 812 to selectively turn on/off the ultraviolet radiation sources 44. However, it is understood that, in order to turn on the ultraviolet radiation sources 44, the computer system 820 can first determine that a device has been securely placed within a housing, receptacle, container, or the like (e.g., via data acquired by one or more sensors 48).

The external interface I/O component 826B can include, for example, a touch screen that can selectively display user interface controls, such as control dials, which can enable the user 812 to adjust one or more of: an intensity, scheduling, and/or other operational properties of the set of ultraviolet radiation sources 44 (e.g., operating parameters, radiation characteristics). In an embodiment, the external interface I/O component 826B could conceivably include a keyboard, a plurality of buttons, a joystick-like control mechanism, and/or the like, which can enable the user 812 to control one or more aspects of the operation of the set of ultraviolet radiation sources 44. The external interface I/O component 826B also can include any combination of various output devices (e.g., an LED, a visual display), which can be operated by the computer system 820 to provide status information pertaining to a cleaning treatment of a medical device for use by the user 812. For example, the external interface I/O component 826B can include one or more LEDs for emitting a visual light for the user 812, e.g., to indicate a status of the ultraviolet treatment of the biological fluid. In an embodiment, the external interface I/O component 826B can include a speaker for providing an alarm (e.g., an auditory signal), e.g., for signaling that ultraviolet radiation is being generated or that a ultraviolet treatment has finished.

The computer system 820 is shown including a processing component 822 (e.g., one or more processors), a storage component 824 (e.g., a storage hierarchy), an input/output (I/O) component 826A (e.g., one or more I/O interfaces and/or devices), and a communications pathway 828. In general, the processing component 822 executes program code, such as the analysis program 830, which is at least partially fixed in the storage component 824. While executing program code, the processing component 822 can process data, which can result in reading and/or writing transformed data from/to the storage component 824 and/or the I/O component 826A for further processing. The pathway 828 provides a communications link between each of the components in the computer system 820. The I/O component 826A and/or the external interface I/O component 826B can comprise one or more human I/O devices, which enable a human user 812 to interact with the computer system 820 and/or one or more communications devices to enable a system user 812 to communicate with the computer system 820 using any type of communications link. To this extent, during execution by the computer system 820, the analysis program 830 can manage a set of interfaces (e.g., graphical user interface(s), application program interface, and/or the like) that enable human and/or system users 812 to interact with the analysis program 830. Furthermore, the analysis program 830 can manage (e.g., store, retrieve, create, manipulate, organize, present, etc.) the data, such as data 840, using any solution.

In any event, the computer system 820 can comprise one or more general purpose computing articles of manufacture (e.g., computing devices) capable of executing program code, such as the analysis program 830, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 830 can be embodied as any combination of system software and/or application software.

Furthermore, the analysis program 830 can be implemented using a set of modules 832. In this case, a module 832 can enable the computer system 820 to perform a set of tasks used by the analysis program 830, and can be separately developed and/or implemented apart from other portions of the analysis program 830. When the computer system 820 comprises multiple computing devices, each computing device can have only a portion of the analysis program 830 fixed thereon (e.g., one or more modules 832). However, it is understood that the computer system 820 and the analysis program 830 are only representative of various possible equivalent monitoring and/or control systems that may perform a process described herein with regard to the control unit, the ultraviolet radiation sources and the sensors. To this extent, in other embodiments, the functionality provided by the computer system 820 and the analysis program 830 can be at least partially be implemented by one or more computing devices that include any combination of general and/or specific purpose hardware with or without program code. In each embodiment, the hardware and program code, if included, can be created using standard engineering and programming techniques, respectively. In another embodiment, the control unit can be implemented without any computing device, e.g., using a closed loop circuit implementing a feedback control loop in which the outputs of one or more sensors are used as inputs to control the operation of the cleaning treatment. Illustrative aspects of the invention are further described in conjunction with the computer system 820. However, it is understood that the functionality described in conjunction therewith can be implemented by any type of monitoring and/or control system.

Regardless, when the computer system 820 includes multiple computing devices, the computing devices can communicate over any type of communications link. Furthermore, while performing a process described herein, the computer system 820 can communicate with one or more other computer systems, such as the user 812, using any type of communications link. In either case, the communications link can comprise any combination of various types of wired and/or wireless links; comprise any combination of one or more types of networks; and/or utilize any combination of various types of transmission techniques and protocols.

All of the components depicted in FIG. 12 can receive power from a power component 845. The power component 845 can take the form of one or more batteries, a vibration power generator that can generate power based on magnetic inducted oscillations or stresses developed on a piezoelectric crystal, a wall plug for accessing electrical power supplied from a grid, and/or the like. In an embodiment, the power source can include a super capacitor that is rechargeable. Other power components that are suitable for use as the power component can include solar, a mechanical energy to electrical energy converter such as a piezoelectric crystal, a rechargeable device, etc.

FIG. 13 shows a schematic of an illustrative environment 900 in which the architecture of the ultraviolet treatment system depicted in FIG. 12 can be used to facilitate a treatment of a biological fluid according to an embodiment. In this embodiment, the computer system 820 of the control unit 46 can be configured to control the ultraviolet radiation sources 44 to direct ultraviolet radiation at a surface of the medical instrument 12 containing biological fluid as described herein. The sensors 48 are configured to acquire data processed by the computer system 820 to monitor a set of attributes regarding the ultraviolet treatment of the biological fluid over a period of time. As illustrated, the sensors 48 can acquire data used by the computer system 820 to monitor the set of attributes (e.g., operating parameters, ultraviolet radiation characteristics).

In the case of determining a presence of biological activity in the biological fluid, a sensor 48 can also determine a location of the biological activity, a type of biological activity (e.g., type of organism), a concentration of the biological activity, an estimated amount of time an organism has been in a growth phase (e.g., exponential growth and/or stationary), and/or the like. Furthermore, a sensor 48 can determine information on the variation of the biological activity over time, such as a growth rate, a rate with which an area including the biological activity is spreading, and/or the like. In an embodiment, a set of biological activity dynamics are related to various attributes of bacteria and/or virus activity present in the biological fluid, including, for example, the presence of detectable bacteria and/or virus activity, measured bacteria and/or virus population/concentration time dynamics, growth phase, and/or the like.

The computer system 820 can be configured to control and adjust a direction, an intensity, a pattern, and/or a spectral power (e.g., wavelength) of the set of ultraviolet radiation sources 44, based on data received from the sensors 48. The computer system 820 can control and adjust each property of the set of ultraviolet radiation sources 44 independently. For example, the computer system 820 can adjust the intensity, time duration, and/or time scheduling (e.g., including duration (e.g., exposure/illumination time)), duty cycle, time between exposures/illuminations, and/or the like) of the ultraviolet radiation source 44 for a given wavelength. Each of the properties of the ultraviolet radiation sources 44 can be adjustable and controlled by the computer system 820 according to data provided by the sensors 48.

For example, the computer system 820 can be configured to adjust the direction of the ultraviolet radiation according to a location of the biological activity detected in the biological fluid using any solution. The computer system 820 can be configured to utilize a target timing, intensity, and/or spectral power of the ultraviolet radiation according to a type of biological activity. That is, the sensors 48 can sense locations of higher levels of biological activity in the biological fluid, and the ultraviolet radiation sources 44 can be configured by the computer system 820 to direct higher doses (by increasing intensity or exposure) of ultraviolet radiation at the locations in the fluid with higher levels of biological activity (e.g., non-uniform ultraviolet radiation).

In one embodiment, the computer system 820 can be configured to set a periodic or an aperiodic schedule for the ultraviolet radiation when the medical device 12 is in place within a housing, receptacle, container or the like that is associated with a need to effectuate an ultraviolet treatment.

As noted above, one of the sensors 48 can include a radiation detector for detecting an amount of radiation with the biological fluid. The radiation can include any type of radiation, including, for example, ultraviolet, visible, infrared, microwave, and/or the like. The amount of radiation to which the surface is exposed can be used by the computer system 820 to determine if any additional radiation is required for disinfection.

It is understood that the environment 900 may include the power component 845 to supply power to one or more of the various components depicted in FIG. 13, such as the ultraviolet radiation sources 44, the sensors 48, the computer system 820, and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system, comprising:
 an ultraviolet impenetrable housing configured to enclose a region having ultraviolet transparent walls, wherein the housing is a flexible sleeve that is configured to wrap around the ultraviolet transparent walls, the flexible sleeve having a fastener closure to secure the housing to the region wrapped there around;
 at least one ultraviolet radiation source integrated within the housing that is configured to emit ultraviolet radiation towards the ultraviolet transparent walls;
 a control unit configured to direct the ultraviolet radiation source to treat the region with ultraviolet radiation, the control unit controlling a plurality of operating parameters for treating the region, the operating parameters including a wavelength of the ultraviolet radiation emitted from the at least one ultraviolet radiation source, an intensity of the ultraviolet radiation delivered to the region by the at least one ultraviolet radiation source and a treatment time that the at least one ultraviolet radiation source delivers the ultraviolet radiation to the region;
 an input component that permits a user to adjust at least one of the plurality of operating parameters; and
 an output component that provides status information of the treatment of the region to the user.

2. The system of claim 1, further comprising an optical element adjacent to the at least one ultraviolet radiation source.

3. The system of claim 2, wherein the optical element comprises a parabolic mirror element formed on an inner surface of the housing, and wherein the at least one ultraviolet radiation source is arranged on the parabolic mirror element.

4. The system of claim 2, wherein optical element comprises at least one light guiding element.

5. The system of claim 4, wherein the light guiding element comprises an ultraviolet transparent fluoropolymer.

6. A system, comprising:
 an ultraviolet impenetrable housing configured to enclose a region having ultraviolet transparent walls, the housing having a first portion, a second portion, and a fastener that couples the first portion to the second portion, forming an extendible insertion opening there between to receive and secure the region;
 at least one ultraviolet radiation source integrated within the housing that is configured to emit ultraviolet radiation towards the region to provide an ultraviolet treatment thereof;
 a control unit configured to direct the at least one ultraviolet radiation source to emit ultraviolet radiation towards the region, the control unit controlling a plurality of operating parameters for treating the region, the operating parameters including a wavelength of the ultraviolet radiation emitted from the at least one ultraviolet radiation source, an intensity of the ultraviolet radiation delivered to the region by the at least one ultraviolet radiation source and a treatment time that the at least one ultraviolet radiation source delivers the ultraviolet radiation to the region;
 an input component that permits a user to adjust at least one of the plurality of operating parameters; and
 an output component that provides status information of the treatment of the region.

7. The system of claim 6, further comprising one or more support elements located along an inner surface of the housing extending outward from the inner surface towards the ultraviolet transparent walls of the region to provide spacing between the region and the inner surface of the housing.

8. The system of claim 7, wherein the one or more support elements and the inner surface of the housing comprise an ultraviolet reflective material for recycling the ultraviolet radiation generated from the at least one ultraviolet radiation source.

9. The system of claim 8, further comprising an optical element adjacent to the at least one ultraviolet radiation source and the one or more support elements, wherein the optical element and the one or more support elements are configured to recycle the ultraviolet radiation generated from the at least one ultraviolet radiation source.

10. The system of claim 6, wherein the at least one ultraviolet radiation source comprises a plurality of ultraviolet light emitting diodes.

11. A device, comprising:
 an ultraviolet impenetrable housing configured to enclose a portion of fluid, wherein the housing comprises an inner chamber having walls with outer and inner sides and an inflow connection and an outflow connection to the fluid, wherein at least some regions within the walls include ultraviolet transparent domains;
 a first device for carrying the fluid to the inner chamber at the inflow connection, wherein the first device is coupled to the inner chamber at the inflow connection;
 a second device for carrying the fluid out of the inner chamber at the outflow connection, wherein the second device is coupled to the outer chamber at the outflow connection;
 at least one ultraviolet radiation source integrated within the housing, wherein the at least one ultraviolet radiation source is adjacent to the outer side of the inner chamber walls in proximity of the ultraviolet transparent domains, the at least one ultraviolet radiation source configured to emit ultraviolet radiation towards and through the ultraviolet transparent domains to the fluid;
 a control unit configured to direct the at least one ultraviolet radiation source to treat the fluid with ultraviolet radiation within the inner chamber, the control unit controlling a plurality of operating parameters for treating the fluid, the operating parameters including a wavelength of the ultraviolet radiation emitted from the at least one ultraviolet radiation source, an intensity of the ultraviolet radiation delivered to the fluid by the at least one ultraviolet radiation source and a treatment time that the at least one ultraviolet radiation source delivers the ultraviolet radiation to the fluid;
 an input component that permits a user to adjust at least one of the plurality of operating parameters; and an output component that provides status information of the treatment of the fluid to the user.

12. The device of claim 11, wherein the ultraviolet transparent domains include a plurality of channels each having a characteristic diameter that is comparable to a light attenuation length scale for a target wavelength to effectuate a treatment of the fluid.

13. The device of claim 12, wherein the characteristic diameter is less than the light attenuation length scale.

14. The device of claim 12, wherein the characteristic diameter is comparable to the ultraviolet light absorption wavelength.

15. The device of claim 11, wherein the inner chamber comprises an ultraviolet transparent material chosen from a group consisting of $SiO_2$, fluoropolymer, $Al_2O_3$, $CaF_2$, and $MgF_2$.

16. The device of claim 11, wherein the housing further comprises an outer chamber having walls with outer and inner sides that surrounds the inner chamber, wherein the at least one ultraviolet radiation source is positioned on the inner side of the outer chamber walls.

17. The device of claim 16, wherein portions of the inner side of the outer chamber walls comprises an ultraviolet reflective material for recycling the ultraviolet radiation generated from the at least one ultraviolet radiation source and an optical element to focus the ultraviolet radiation emitted from the ultraviolet radiation source to the fluid.

18. The device of claim 11, wherein the inner chamber comprises a cylindrical chamber.

19. The device of claim 11, wherein the first device comprises a first tube carrying the fluid and the second device comprises a second tube carrying the fluid, and wherein each of the inflow connection and the outflow connection of the inner chamber comprises inserts for respective placement within the first tube and the second tube.

20. The device of claim 11, wherein the first device comprises a first tube carrying the fluid and the second device comprises a second tube carrying the fluid, and wherein each of the inflow connection and the outflow connection comprise cavities adapted for respective insertion of the first tube and the second tube.

* * * * *